United States Patent
Raynaud et al.

(10) Patent No.: US 11,655,486 B2
(45) Date of Patent: May 23, 2023

(54) MICROORGANISM AND METHOD FOR IMPROVED 1,3-PROPANEDIOL PRODUCTION BY FERMENTATION ON A CULTURE MEDIUM WITH HIGH GLYCERINE CONTENT

(71) Applicant: METABOLIC EXPLORER, Saint Beauzire (FR)

(72) Inventors: Céline Raynaud, Saint Beauzire (FR); Olivier Tourrasse, Les Martres de Veyre (FR); Nadège Dumoulin, Gerzat (FR)

(73) Assignee: METABOLIC EXPLORER, Saint Beauzire (FR)

(*) Notice: Subject to any disclaimer, the term of this patent is extended or adjusted under 35 U.S.C. 154(b) by 194 days.

(21) Appl. No.: 16/636,237

(22) PCT Filed: Aug. 3, 2018

(86) PCT No.: PCT/EP2018/071104
§ 371 (c)(1),
(2) Date: Feb. 3, 2020

(87) PCT Pub. No.: WO2019/025580
PCT Pub. Date: Feb. 7, 2019

(65) Prior Publication Data
US 2020/0370072 A1    Nov. 26, 2020

(30) Foreign Application Priority Data
Aug. 4, 2017   (EP) .................................. 17306044

(51) Int. Cl.
*C12P 7/18*     (2006.01)
*C12N 1/20*     (2006.01)
*C12R 1/22*     (2006.01)
*C12R 1/145*    (2006.01)

(52) U.S. Cl.
CPC .............. *C12P 7/18* (2013.01); *C12N 1/205* (2021.05); *C12R 2001/145* (2021.05); *C12R 2001/22* (2021.05)

(58) Field of Classification Search
CPC . C12P 7/18; C12R 2001/22; C12R 2001/145; C12N 1/205; C12N 1/36
See application file for complete search history.

(56) References Cited

U.S. PATENT DOCUMENTS 8,236,994 B2 * 8/2012 Soucaille ...................... 568/852

FOREIGN PATENT DOCUMENTS

| EP | 1 892 300 A1 | 2/2008 |
|---|---|---|
| WO | WO 01/04324 A1 | 1/2001 |
| WO | WO 2006/128381 A1 | 12/2006 |
| WO | WO 2009/068110 A1 | 6/2009 |
| WO | WO 2010/037843 A1 | 4/2010 |
| WO | WO 2010/128070 A2 | 11/2010 |
| WO | WO 2011/042434 A1 | 4/2011 |
| WO | WO 2012/062832 A1 | 5/2012 |

OTHER PUBLICATIONS

Altschul et al., "Basic Local Alignment Search Tool", J. Mol. Biol., vol. 215, 1990, pp. 403-410.
Chambers et al., "The pMTL nic—cloning vectors. I. Improved pUC polylinker regions to facilitate the use of sonicated DNA for nucleotide sequencing", Gene, vol. 68, 1988, pp. 139-149.
Davis et al., "Characterizing the Native Codon Usages of a Genome: An Axis Projection Approach", Mol. Biol. Evol., vol. 28, No. 1, 2011, pp. 211-221.
Deml et al., "Multiple Effects of Codon Usage Optimization on Expression and Immunogenicity of DNA Candidate Vaccines Encoding the Human Immunodeficiency Virus Type 1 Gag Protein", Journal of Virology, vol. 75, No. 22, Nov. 2001, pp. 10991-11001.
European Search Report dated Jan. 10, 2018, for corresponding European Application No. 17306044.
González-Pajuelo et al., "Metabolic engineering of Clostridium acetobutylicum for the industrial production of 1,3-propanediol from glycerol", Metabolic Engineering, vol. 7, 2005, pp. 329-336.
González-Pajuelo et al., Microbial Conversion of Glycerol to 1,3-Propanediol: Physiological Comparison of a Natural Producer, Clostridium butyricum VPI 3266, and an Engineered Strain, Clostridium acetobutylicum DG1(pSPD5), Applied and Environmental Microbiology, vol. 72, No. 1, Jan. 2006 pp. 96-101.
Graf et al., "Concerted Action of Multiple cis-Acting Sequences is Required for Rev Dependence of Late Human Immunodeficiency Virus Type 1 Gene Expression", Journal of Virology, vol. 74, No. 22, Nov. 2000, pp. 10822-10826.
International Search Report dated Nov. 2, 2018, for International Application No. PCT/EP2018/071104.
Lee et al., "Construction of *Escherichia coli*-clostridium Acetobutylicum Shuttle Vectors and Transformation of Clostridium Acetobutylicum Strains", Biotechnology Letters, vol. 14, No. 5, May 1992, pp. 427-432.
Papanikolaou et al., "High production of 1,3-propanediol from industrial glycerol by a newly isolated Clostridium butyricum strain", Journal of Biotechnology, vol. 77, 2000, pp. 191-208.

(Continued)

*Primary Examiner* — Satyendra K Singh
(74) *Attorney, Agent, or Firm* — Birch, Stewart, Kolasch & Birch, LLP

(57) ABSTRACT

The present invention concerns a new method for the production of 1,3-propanediol comprising culturing a recombinant microorganism converting glycerol into 1,3-propanediol and overexpressing the hcpR and/or frdX gene on a medium comprising glycerine. A recombinant microorganism for the production of 1,3 propanediol from glycerol, wherein said microorganism converts glycerol into 1,3-propanediol and 10 overexpresses the hcpR and/or the frdX gene.

9 Claims, 2 Drawing Sheets

Figure 1:
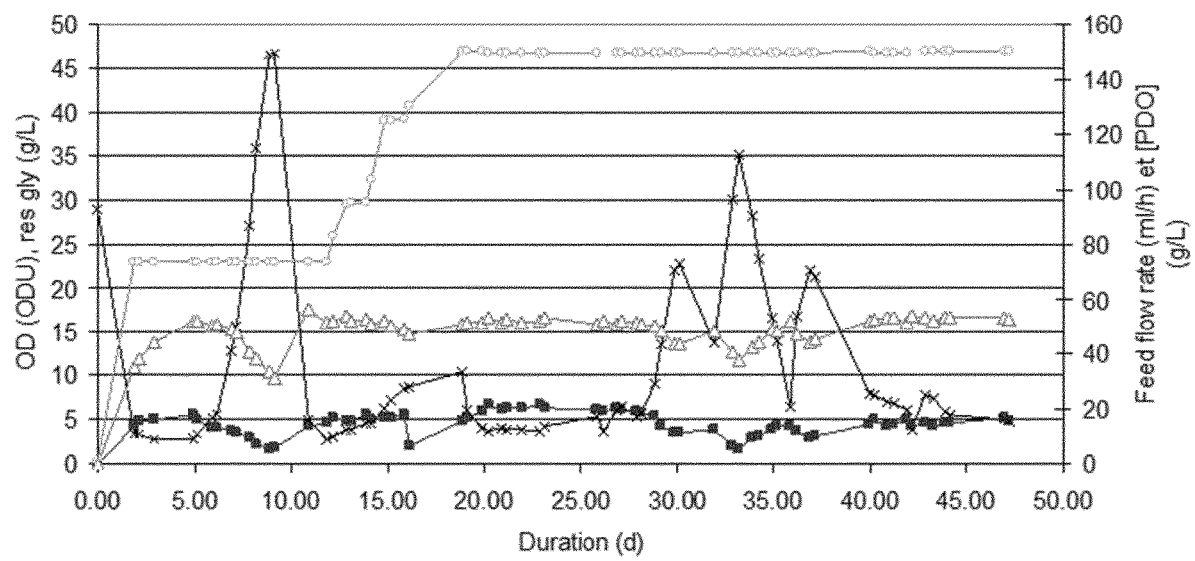

Specification includes a Sequence Listing.

(56) References Cited

OTHER PUBLICATIONS

Tummala et al., "Development and Characterization of a Gene Expression Reporter System for Clostridium acetobutylicum ATCC 824", Applied and Environmental Microbiology, vol. 65, No. 9, Sep. 1999, pp. 3793-3799.

Vasconcelos et al., "Regulation of Carbon and Electron Flow in Clostridium acetobutylicum Grown in Chemostat Culture at Neutral pH on Mixtures of Glucose and Glycerol", Journal of Bacteriology, vol. 176, No. 3, Mar. 1994, pp. 1443-1450.

\* cited by examiner

SEQUENCE LISTING

```
<160> NUMBER OF SEQ ID NOS: 25

<210> SEQ ID NO 1
<211> LENGTH: 690
<212> TYPE: DNA
<213> ORGANISM: Clostridium acetobutylicum
<220> FEATURE:
<221> NAME/KEY: misc_feature
<223> OTHER INFORMATION: CA_C0884 gene sequence

<400> SEQUENCE: 1
atggataaaa aaattttaac cgtattaaaa cattgtatct tattttcaaa aattgaaact      60
caggaaattg atcatttatt ttcatctata aattactcaa taaaagaata ctataaagat     120
gaaactatcg caattgaagg cgatacgtgc aataaaattg gaatagtatt aagcggttgt     180
gttgaaatac agaaaattta cgaatctggt aaaagtctta caataacaac actagaagaa     240
agcaagatat ttggtgaagc aataatattc tccaataaaa caagctatcc ttctacaata     300
atagcatgta ctaaaagtac tataatttt attcccaaag cctcaatatc taaattatgc     360
agcgacaatt cccttttcct taatggcttt atgtctcttc tatctaataa gatattgatg     420
ttgaataaaa aattaaaaaa tatgtcttat catactataa gagagaaaat atcaaactat     480
atacttgaac agtacgaagc tcaaaataac ttaacttttta aaatgaataa gtcaaaaaaa     540
cagttgtctg aaatgcttgg aattccaagg ccatcattat ctagagaatt cataaaccta     600
cgtgaagaag gaattataga ctttgataga acatctatta caatattaga tattaactct     660
ttaaaagaaa ttttagaagc tgcagaataa                                     690

<210> SEQ ID NO 2
<211> LENGTH: 229
<212> TYPE: PRT
<213> ORGANISM: Clostridium acetobutylicum
<220> FEATURE:
<221> NAME/KEY: MISC_FEATURE
<223> OTHER INFORMATION: CA_C0884 protein sequence : NP_347520.1
```

<400> SEQUENCE: 2

```
Met Asp Lys Lys Ile Leu Thr Val Leu Lys His Cys Ile Leu Phe Ser
1               5                   10                  15

Lys Ile Glu Thr Gln Glu Ile Asp His Leu Phe Ser Ser Ile Asn Tyr
            20                  25                  30

Ser Ile Lys Glu Tyr Tyr Lys Asp Glu Thr Ile Ala Ile Glu Gly Asp
        35                  40                  45

Thr Cys Asn Lys Ile Gly Ile Val Leu Ser Gly Cys Val Glu Ile Gln
    50                  55                  60

Lys Ile Tyr Glu Ser Gly Lys Ser Leu Thr Ile Thr Thr Leu Glu Glu
65                  70                  75                  80

Ser Lys Ile Phe Gly Glu Ala Ile Ile Phe Ser Asn Lys Thr Ser Tyr
                85                  90                  95

Pro Ser Thr Ile Ile Ala Cys Thr Lys Ser Thr Ile Ile Phe Ile Pro
            100                 105                 110

Lys Ala Ser Ile Ser Lys Leu Cys Ser Asp Asn Ser Leu Phe Leu Asn
        115                 120                 125

Gly Phe Met Ser Leu Leu Ser Asn Lys Ile Leu Met Leu Asn Lys Lys
    130                 135                 140

Leu Lys Asn Met Ser Tyr His Thr Ile Arg Glu Lys Ile Ser Asn Tyr
145                 150                 155                 160

Ile Leu Glu Gln Tyr Glu Ala Gln Asn Asn Leu Thr Phe Lys Met Asn
                165                 170                 175

Lys Ser Lys Lys Gln Leu Ser Glu Met Leu Gly Ile Pro Arg Pro Ser
            180                 185                 190

Leu Ser Arg Glu Phe Ile Asn Leu Arg Glu Glu Gly Ile Ile Asp Phe
        195                 200                 205

Asp Arg Thr Ser Ile Thr Ile Leu Asp Ile Asn Ser Leu Lys Glu Ile
    210                 215                 220

Leu Glu Ala Ala Glu
225
```

<210> SEQ ID NO 3
<211> LENGTH: 711
<212> TYPE: DNA
<213> ORGANISM: Clostridium acetobutylicum
<220> FEATURE:
<221> NAME/KEY: misc_feature
<223> OTHER INFORMATION: CA_C0885 gene sequence

<400> SEQUENCE: 3

```
atgaaaagaa aaatagtaaa catagataaa gataaatgta atggatgtgg actttgtagt      60
gaagcatgtc atgaaaatgc aattgaaata attaatggaa aagcagagct tttatctgat     120
gaatattgtg atggtttagg agattgttta cctcattgtc agttgatgc aataactata     180 atagagagag aaagtaagga atatgatgaa gaggcagttc agagaagaat tgaagaaaag     240
aaaaaatcaa agttagctaa accctgtgga tgtccaggag ctatggctaa aaaaatagaa     300
agagtagcta agcctttagc taaagtaaag gaagataggt cttctgtttc agagttaatg     360
cagtggccag ttcagttaag gcttgtaagt ccaggagctc atattttaa aaatgctaat     420 cttttagtag ctgcagattg tacagcctat gcttatggtg actttcacaa tgatttata     480 aagaatcata taacagtaat aggatgtcca aaacttgatg atgttacata ttacaaagat     540
aagttgaaag aaattataga acttaatgac cttaagagta taacagttgt tagaatggag     600
```

```
gtaccttgct gttcaggcat agtttcagca gtaaagactg ctatgcttga agcaaaagtt        660
atagtacctt ttagagaagt tattatagga actaatggtg aaattagata a                711
```

<210> SEQ ID NO 4
<211> LENGTH: 236
<212> TYPE: PRT
<213> ORGANISM: Clostridium acetobutylicum
<220> FEATURE:
<221> NAME/KEY: MISC_FEATURE
<223> OTHER INFORMATION: CA_C0885 protein sequence : NP_347521.1

<400> SEQUENCE: 4

```
Met Lys Arg Lys Ile Val Asn Ile Asp Lys Asp Lys Cys Asn Gly Cys
1               5                   10                  15

Gly Leu Cys Ser Glu Ala Cys His Glu Asn Ala Ile Glu Ile Ile Asn
            20                  25                  30

Gly Lys Ala Glu Leu Leu Ser Asp Glu Tyr Cys Asp Gly Leu Gly Asp
        35                  40                  45

Cys Leu Pro His Cys Pro Val Asp Ala Ile Thr Ile Ile Glu Arg Glu
    50                  55                  60

Ser Lys Glu Tyr Asp Glu Glu Ala Val Gln Arg Arg Ile Glu Glu Lys
65                  70                  75                  80

Lys Lys Ser Lys Leu Ala Lys Pro Cys Gly Cys Pro Gly Ala Met Ala
                85                  90                  95

Lys Lys Ile Glu Arg Val Ala Lys Pro Leu Ala Lys Val Lys Glu Asp
            100                 105                 110

Arg Ser Ser Val Ser Glu Leu Met Gln Trp Pro Val Gln Leu Arg Leu
        115                 120                 125

Val Ser Pro Gly Ala Pro Tyr Phe Lys Asn Ala Asn Leu Leu Val Ala
    130                 135                 140

Ala Asp Cys Thr Ala Tyr Ala Tyr Gly Asp Phe His Asn Asp Phe Ile
145                 150                 155                 160

Lys Asn His Ile Thr Val Ile Gly Cys Pro Lys Leu Asp Asp Val Thr
                165                 170                 175

Tyr Tyr Lys Asp Lys Leu Lys Glu Ile Ile Glu Leu Asn Asp Leu Lys
            180                 185                 190

Ser Ile Thr Val Val Arg Met Glu Val Pro Cys Cys Ser Gly Ile Val
        195                 200                 205

Ser Ala Val Lys Thr Ala Met Leu Glu Ala Lys Val Ile Val Pro Phe
    210                 215                 220

Arg Glu Val Ile Ile Gly Thr Asn Gly Glu Ile Arg
225                 230                 235
```

<210> SEQ ID NO 5
<211> LENGTH: 684
<212> TYPE: DNA
<213> ORGANISM: Clostridium pasteurianum
<220> FEATURE:
<221> NAME/KEY: misc_feature
<223> OTHER INFORMATION: BEE63_RS05095 gene sequence

<400> SEQUENCE: 5

```
atggataaag aactttttaag tatattaaag aactgtattt tattttgcaa aattgatgat        60
actaaaatta atgagctttt ttcatatata aattattcaa taaaaaaata ctcaaatgga       120
gaaactgtgg ccattgaagg tgacgagtgc agcagcatag gtataatttt agacggtttt       180
gctgagatac aaaaaatcta cgaatccggc aaaagtttaa ctatagagac cttaaacact       240
```

```
aacaagatat tggtgaagc aataatattt tctaaaaaaa atacttatcc ggctacaata    300
atttcatgtg ccaaaacaag tatattattc ataccaaaat cctcaataat taaattatgc   360
agcgaaaatt caaattttct aaacggcttt atgtctcttc tatctaataa aatattaatg   420
ctaaataaaa agttaaaaaa tcttctcatat aacacaatta gagaaaaagt agcaaattac  480
ctacttgaag agactataat ccaaaaaaat ccaaatataa aaatgaataa atcaaaaaaa   540
cagctgtctg aattactcgg tattccacgt ccttctctgt ctagagaatt aataaagtta   600
aggaacgatg gtatcatttc ctttgataga aattatatta aaatattaaa tatggatgag   660
ttaaaaaata tcctagataa gtag                                          684
```

```
<210> SEQ ID NO 6
<211> LENGTH: 227
<212> TYPE: PRT
<213> ORGANISM: Clostridium pasteurianum
<220> FEATURE:
<221> NAME/KEY: MISC_FEATURE
<223> OTHER INFORMATION: BEE63_RS05095 protein sequence : WP_066020350

<400> SEQUENCE: 6

Met Asp Lys Glu Leu Leu Ser Ile Leu Lys Asn Cys Ile Leu Phe Cys
 1               5                  10                  15

Lys Ile Asp Asp Thr Lys Ile Asn Glu Leu Phe Ser Tyr Ile Asn Tyr
            20                  25                  30

Ser Ile Lys Lys Tyr Ser Asn Gly Glu Thr Val Ala Ile Glu Gly Asp
        35                  40                  45

Glu Cys Ser Ser Ile Gly Ile Ile Leu Asp Gly Phe Ala Glu Ile Gln
    50                  55                  60

Lys Ile Tyr Glu Ser Gly Lys Ser Leu Thr Ile Glu Thr Leu Asn Thr
65                  70                  75                  80

Asn Lys Ile Phe Gly Glu Ala Ile Ile Phe Ser Lys Lys Asn Thr Tyr
                85                  90                  95

Pro Ala Thr Ile Ile Ser Cys Ala Lys Thr Ser Ile Leu Phe Ile Pro
           100                 105                 110

Lys Ser Ser Ile Ile Lys Leu Cys Ser Glu Asn Ser Asn Phe Leu Asn
       115                 120                 125

Gly Phe Met Ser Leu Leu Ser Asn Lys Ile Leu Met Leu Asn Lys Lys
   130                 135                 140

Leu Lys Asn Leu Ser Tyr Asn Thr Ile Arg Glu Lys Val Ala Asn Tyr
145                 150                 155                 160

Leu Leu Glu Glu Thr Ile Ile Gln Lys Asn Pro Asn Ile Lys Met Asn
                165                 170                 175

Lys Ser Lys Lys Gln Leu Ser Glu Leu Leu Gly Ile Pro Arg Pro Ser
            180                 185                 190

Leu Ser Arg Glu Leu Ile Lys Leu Arg Asn Asp Gly Ile Ile Ser Phe
        195                 200                 205

Asp Arg Asn Tyr Ile Lys Ile Leu Asn Met Asp Glu Leu Lys Asn Ile
    210                 215                 220

Leu Asp Lys
225
```

```
<210> SEQ ID NO 7
<211> LENGTH: 690
<212> TYPE: DNA
<213> ORGANISM: Clostridium butyricum
<220> FEATURE:
<221> NAME/KEY: misc_feature
```

<223> OTHER INFORMATION: CBY_RS14495 gene sequence

<400> SEQUENCE: 7

```
atgaaaaatg ttaatgagat tatagataaa ataaagcaaa atgaattttt taagggata      60
gatgataaaa aaatagaaat gattatttca gaattaagtc atatttctaa ggaatattca    120
aaaggacagg taattgctaa tgaggggag gtttgtaaaa atctaggatt agtcgtagat     180
ggaattgttg agatacagag aatatactca agcggaaaac atatagttct taaacgtatg    240
ggagcaggag aagttttgg agaagccata atattttcag ataaaaataa atatccagcc     300
acaataattg cttcttcgga ttgtataata tcttatttga aaaagaaga tattattaaa     360
ctttgcctta atgaagaaat aatcttaaag aattttataa ctttattgag caataaaatt    420
tttatattaa atagaaaaat aaaaaccata tcttttaaaa caatacgaca gaaagttgtt    480
aactttatat tagaacagtc aaaaagtcag aacaataaaa ctgtaatttt gaaaataagt    540
aaagagcaga tagcatcttt acttggaata cctagaccat cactttcaag agagcttatg    600
aagcttagag atgatggact tattgaattt gataggaaca aataagtat tataaatata     660
gaaagacttg aagaagaact tttagaatag                                      690
```

<210> SEQ ID NO 8
<211> LENGTH: 229
<212> TYPE: PRT
<213> ORGANISM: Clostridium butyricum
<220> FEATURE:
<221> NAME/KEY: MISC_FEATURE
<223> OTHER INFORMATION: CBY_RS14495 protein sequence : WP_003410673.1

<400> SEQUENCE: 8

```
Met Lys Asn Val Asn Glu Ile Ile Asp Lys Ile Lys Gln Asn Glu Phe
1               5                   10                  15

Phe Lys Gly Ile Asp Asp Lys Lys Ile Glu Met Ile Ile Ser Glu Leu
            20                  25                  30

Ser His Ile Ser Lys Glu Tyr Ser Lys Gly Gln Val Ile Ala Asn Glu
        35                  40                  45

Gly Glu Val Cys Lys Asn Leu Gly Leu Val Val Asp Gly Ile Val Glu
    50                  55                  60

Ile Gln Arg Ile Tyr Ser Ser Gly Lys His Ile Val Leu Lys Arg Met
65                  70                  75                  80

Gly Ala Gly Glu Val Phe Gly Glu Ala Ile Ile Phe Ser Asp Lys Asn
                85                  90                  95

Lys Tyr Pro Ala Thr Ile Ile Ala Ser Ser Asp Cys Ile Ile Ser Tyr
            100                 105                 110

Leu Lys Lys Glu Asp Ile Ile Lys Leu Cys Leu Asn Glu Glu Ile Ile
        115                 120                 125

Leu Lys Asn Phe Ile Thr Leu Leu Ser Asn Lys Ile Phe Ile Leu Asn
    130                 135                 140

Arg Lys Ile Lys Thr Ile Ser Phe Lys Thr Ile Arg Gln Lys Val Val
145                 150                 155                 160

Asn Phe Ile Leu Glu Gln Ser Lys Ser Gln Asn Asn Lys Thr Val Ile
                165                 170                 175

Leu Lys Ile Ser Lys Glu Gln Ile Ala Ser Leu Leu Gly Ile Pro Arg
            180                 185                 190

Pro Ser Leu Ser Arg Glu Leu Met Lys Leu Arg Asp Asp Gly Leu Ile
        195                 200                 205

Glu Phe Asp Arg Asn Lys Ile Ser Ile Ile Asn Ile Glu Arg Leu Glu
```

Glu Glu Leu Leu Glu
225

<210> SEQ ID NO 9
<211> LENGTH: 690
<212> TYPE: DNA
<213> ORGANISM: Clostridium butyricum
<220> FEATURE:
<221> NAME/KEY: misc_feature
<223> OTHER INFORMATION: K670_RS19640 gene sequence

<400> SEQUENCE: 9

```
atgaaaaatg ctaatgagat tatagataaa ataaagcaaa atgaattttt taagggata      60
gatgataaaa aaatagaaat gattatttca gaattaagtc atatttctaa ggaatattca    120
aaaggacagg taattgctaa tgaggggag gtttgtaaaa atctaggatt agtcgtagat     180
ggaattgttg agatacagag aatatactca agcggaaaac atatagttct aaacgtatg    240
ggagcaggag aagtttttgg agaagccata atattttcag ataaaaataa atatccagcc   300
acaataattg cttcttcgga ttgtataata tcttatttga aaaagaaga tattattaaa    360
ctttgcctta atgaagaaat aatttttaaag aattttataa ctttattgag caataaaatt   420
tttatattaa atagaaaaat aaaaaccata tcttttaaaa caatacgaca gaaagttgtt    480
aactttatat tagaacagtc aaaaagtcag aacaataaaa ctgtaatttt gaaaataagt    540
aaagagcaga tagcatcttt acttggaata cctagaccat cactttcaag agagcttatg   600
aaacttagag atgatggact tattgaattt gataggaaca aataagtat tataaatata    660
gaaagacttg aagaagaact tttagaatag                                     690
```

<210> SEQ ID NO 10
<211> LENGTH: 229
<212> TYPE: PRT
<213> ORGANISM: Clostridium butyricum
<220> FEATURE:
<221> NAME/KEY: MISC_FEATURE
<223> OTHER INFORMATION: K670_RS19640 protein sequence : WP_035765453.1

<400> SEQUENCE: 10

Met Lys Asn Ala Asn Glu Ile Ile Asp Lys Ile Lys Gln Asn Glu Phe
1               5                   10                  15

Phe Lys Gly Ile Asp Asp Lys Lys Ile Glu Met Ile Ile Ser Glu Leu
            20                  25                  30

Ser His Ile Ser Lys Glu Tyr Ser Lys Gly Gln Val Ile Ala Asn Glu
        35                  40                  45

Gly Glu Val Cys Lys Asn Leu Gly Leu Val Val Asp Gly Ile Val Glu
    50                  55                  60

Ile Gln Arg Ile Tyr Ser Ser Gly Lys His Ile Val Leu Lys Arg Met
65                  70                  75                  80

Gly Ala Gly Glu Val Phe Gly Glu Ala Ile Ile Phe Ser Asp Lys Asn
                85                  90                  95

Lys Tyr Pro Ala Thr Ile Ile Ala Ser Ser Asp Cys Ile Ile Ser Tyr
            100                 105                 110

Leu Lys Lys Glu Asp Ile Ile Lys Leu Cys Leu Asn Glu Glu Ile Ile
        115                 120                 125

Leu Lys Asn Phe Ile Thr Leu Leu Ser Asn Lys Ile Phe Ile Leu Asn
    130                 135                 140

Arg Lys Ile Lys Thr Ile Ser Phe Lys Thr Ile Arg Gln Lys Val Val

| | | | | | | | | | | | |
|---|---|---|---|---|---|---|---|---|---|---|---|
|145| | | | |150| | | | |155| |160|

Asn Phe Ile Leu Glu Gln Ser Lys Ser Gln Asn Asn Lys Thr Val Ile
                165                        170                   175

Leu Lys Ile Ser Lys Glu Gln Ile Ala Ser Leu Leu Gly Ile Pro Arg
                180                        185                   190

Pro Ser Leu Ser Arg Glu Leu Met Lys Leu Arg Asp Gly Leu Ile
                195                        200                   205

Glu Phe Asp Arg Asn Lys Ile Ser Ile Ile Asn Ile Glu Arg Leu Glu
                210                        215                   220

Glu Glu Leu Leu Glu
225

<210> SEQ ID NO 11
<211> LENGTH: 690
<212> TYPE: DNA
<213> ORGANISM: Clostridium butyricum
<220> FEATURE:
<221> NAME/KEY: misc_feature
<223> OTHER INFORMATION: AT697_RS15885 gene sequence

<400> SEQUENCE: 11

```
atgaaaaatg ttaatgagat tatagataaa ataaagcaaa atgaattttt taaggggata    60
gatgataaaa aaatagaaat gattatttca gaattaagtc atatttataa ggaatattca   120
aaaggacagg taattgctaa tgaggggag gtttgtaaaa atctaggatt agtcgtagat    180
ggaattgttg agatacagag aatatactca agcggaaaac atatagttct taaacgtatg   240
ggagcaggag aagtttttgg agaagccata atattttcag ataaaaataa atatccagcc   300
acaataattg cttcttcgga ttgtataata tcttatttga aaaagaaga tattattaaa   360
ctttgcctta tgaagaaat aatcttaaag aattttataa ctttattgag caataaaatt   420
tttatattaa atagaaaaat aaaaaccata tcttttaaaa caatacgaca gaaagttgtt   480
aactttatat tagaacagtc aaaaagtcag aacaataaaa ctgtaatttt gaaataagt   540
aaagagcaga tagcatcttt acttggaata cctagaccat cactttcaag agagcttatg   600
aagcttagag atgatggact tattgaattt gataggaaca aaataagtat tataaatata   660
gaaagacttg aagaagagct tttagaatag                                    690
```

<210> SEQ ID NO 12
<211> LENGTH: 229
<212> TYPE: PRT
<213> ORGANISM: Clostridium butyricum
<220> FEATURE:
<221> NAME/KEY: MISC_FEATURE
<223> OTHER INFORMATION: AT697_RS15885 protein sequence : WP_046057470.1

<400> SEQUENCE: 12

Met Lys Asn Val Asn Glu Ile Ile Asp Lys Ile Lys Gln Asn Glu Phe
1                5                    10                   15

Phe Lys Gly Ile Asp Asp Lys Lys Ile Glu Met Ile Ile Ser Glu Leu
                20                        25                   30

Ser His Ile Tyr Lys Glu Tyr Ser Lys Gly Gln Val Ile Ala Asn Glu
                35                        40                   45

Gly Glu Val Cys Lys Asn Leu Gly Leu Val Val Asp Gly Ile Val Glu
                50                        55                   60

Ile Gln Arg Ile Tyr Ser Ser Gly Lys His Ile Val Leu Lys Arg Met
65               70                    75                   80

Gly Ala Gly Glu Val Phe Gly Glu Ala Ile Ile Phe Ser Asp Lys Asn 85                  90                  95
Lys Tyr Pro Ala Thr Ile Ile Ala Ser Ser Asp Cys Ile Ile Ser Tyr
            100                 105                 110

Leu Lys Lys Glu Asp Ile Ile Lys Leu Cys Leu Asn Glu Glu Ile Ile
        115                 120                 125

Leu Lys Asn Phe Ile Thr Leu Leu Ser Asn Lys Ile Phe Ile Leu Asn
    130                 135                 140

Arg Lys Ile Lys Thr Ile Ser Phe Lys Thr Ile Arg Gln Lys Val Val
145                 150                 155                 160

Asn Phe Ile Leu Glu Gln Ser Lys Ser Gln Asn Asn Lys Thr Val Ile
                165                 170                 175

Leu Lys Ile Ser Lys Glu Gln Ile Ala Ser Leu Leu Gly Ile Pro Arg
            180                 185                 190

Pro Ser Leu Ser Arg Glu Leu Met Lys Leu Arg Asp Asp Gly Leu Ile
        195                 200                 205

Glu Phe Asp Arg Asn Lys Ile Ser Ile Ile Asn Ile Glu Arg Leu Glu
    210                 215                 220

Glu Glu Leu Leu Glu
225

<210> SEQ ID NO 13
<211> LENGTH: 711
<212> TYPE: DNA
<213> ORGANISM: Clostridium pasteurianum
<220> FEATURE:
<221> NAME/KEY: misc_feature
<223> OTHER INFORMATION: BEE63_RS05090 gene sequence

<400> SEQUENCE: 13
atgaaaagaa aaatagtgaa atatagataaa gaaaaatgta atggatgtgg actttgtagt      60
aaggcatgcc atgaaaatgc tatagaaata attgatggaa aagcagaact tgtttcggat     120
gaatattgtg atggacttgg agattgcctt ccacattgtc cagaaaacgc tataactata     180
atagaaagag aaagtaaaga atacgatgaa gaagctgtaa aagaagaat tgaaagtaaa      240 gaaaagaaaa tgccatgtgg atgtccaggt tcaatggcaa aaaagataac tagagttcct     300
aaaaaagtag aagttaaaca tgaagatacg ggtgcagcat cagaacttat gcagtggcct     360
gtacaattgc aattagtaaa tccaaatgca agctattttg aaggcgcaaa tcttttagtt     420
gcagcggatt gtacagctta tgcttatggt aactttcatc aagattttat aaaaaatcat     480
ataactgtaa taggttgtcc taaacttgac gatgttgagt actataagaa taaaatcaaa     540
gaaattatag aaaataataa tcttaaaagt attacagtta ccagaatgga agtaccatgc     600
tgtggcggta tagtgtcagc tgtaaagaat gctatgcttg aggcacaggt tatattacct     660
tatagagaag tagttatagg aactaatgga gaagtgaagg aagcgaagta a               711

<210> SEQ ID NO 14
<211> LENGTH: 236
<212> TYPE: PRT
<213> ORGANISM: Clostridium pasteurianum
<220> FEATURE:
<221> NAME/KEY: MISC_FEATURE
<223> OTHER INFORMATION: BEE63_RS05090 protein sequence : WP_066020349.1

<400> SEQUENCE: 14

Met Lys Arg Lys Ile Val Asn Ile Asp Lys Glu Lys Cys Asn Gly Cys
1               5                   10                  15

Gly Leu Cys Ser Lys Ala Cys His Glu Asn Ala Ile Glu Ile Ile Asp

```
                     20                  25                  30
Gly Lys Ala Glu Leu Val Ser Asp Glu Tyr Cys Asp Gly Leu Gly Asp
                 35                  40                  45

Cys Leu Pro His Cys Pro Glu Asn Ala Ile Thr Ile Ile Glu Arg Glu
             50                  55                  60

Ser Lys Glu Tyr Asp Glu Ala Val Lys Arg Arg Ile Glu Ser Lys
 65                  70                  75                  80

Glu Lys Lys Met Pro Cys Gly Cys Pro Gly Ser Met Ala Lys Lys Ile
                 85                  90                  95

Thr Arg Val Ser Lys Lys Val Glu Val Lys His Glu Asp Thr Gly Ala
             100                 105                 110

Ala Ser Glu Leu Met Gln Trp Pro Val Gln Leu Gln Leu Val Asn Pro
         115                 120                 125

Asn Ala Ser Tyr Phe Glu Gly Ala Asn Leu Leu Val Ala Ala Asp Cys
     130                 135                 140

Thr Ala Tyr Ala Tyr Gly Asn Phe His Gln Asp Phe Ile Lys Asn His
145                 150                 155                 160

Ile Thr Val Ile Gly Cys Pro Lys Leu Asp Asp Val Glu Tyr Tyr Lys
                 165                 170                 175

Asn Lys Ile Lys Glu Ile Ile Glu Asn Asn Asn Leu Lys Ser Ile Thr
             180                 185                 190

Val Thr Arg Met Glu Val Pro Cys Cys Gly Gly Ile Val Ser Ala Val
         195                 200                 205

Lys Asn Ala Met Leu Glu Ala Gln Val Ile Leu Pro Tyr Arg Glu Val
     210                 215                 220

Val Ile Gly Thr Asn Gly Glu Val Lys Glu Ala Lys
225                 230                 235
```

<210> SEQ ID NO 15
<211> LENGTH: 1524
<212> TYPE: DNA
<213> ORGANISM: Clostridium acetobutylicum
<220> FEATURE:
<221> NAME/KEY: misc_feature
<223> OTHER INFORMATION: Full sequence comprising CA_C0884, the
      intergenic region, and CA_C0885

<400> SEQUENCE: 15

```
ttattctgca gcttctaaaa tttcttttaa agagttaata tctaatattg taatagatgt      60
tctatcaaag tctataattc cttcttcacg taggtttatg aattctctag ataatgatgg     120
ccttggaatt ccaagcattt cagacaactg ttttttttgac ttattcattt taaaagttaa    180
gttattttga gcttcgtact gttcaagtat atagtttgat attttctctc ttatagtatg     240
ataagacata tttttttaatt ttttattcaa catcaatatc ttattagata gaagagacat    300
aaagccatta aggaaaaggg aattgtcgct gcataattta gatattgagg ctttgggaat     360
aaaaattata gtacttttag tacatgctat tattgtagaa ggatagcttg ttttattgga    420
gaatatatt gcttcaccaa atatcttgct ttcttctagt gttgttattg taagactttt     480
accagattcg taaattttct gtatttcaac acaaccgctt aatactattc caatttttatt   540
gcacgtatcg ccttcaattg cgatagtttc atctttatag tattctttta ttgagtaatt    600
tatagatgaa ataaatgat caatttcctg agtttcaatt tttgaaaata agatacaatg     660
ttttaatacg gttaaaattt ttttatccat gttttctcc caatactttt ttgtgtaaca     720
tatgttactg atatatttat ataatttttaa tataatttttaa tcataaagac aagtaatttt 780
```

-continued

```
attttgcgga actttatatt taggaggaaa aaaatgaaaa gaaaaatagt aaacatagat      840
aaagataaat gtaatggatg tggactttgt agtgaagcat gtcatgaaaa tgcaattgaa      900
ataattaatg aaaagcaga gcttttatct gatgaatatt gtgatggttt aggagattgt      960
ttacctcatt gtccagttga tgcaataact ataatagaga gagaaagtaa ggaatatgat      1020
gaagaggcag ttcagagaag aattgaagaa aagaaaaaat caaagttagc taaaccctgt     1080
ggatgtccag gagctatggc taaaaaaata gaaagagtag ctaagccttt agctaaagta     1140
aaggaagata ggtcttctgt ttcagagtta atgcagtggc cagttcagtt aaggcttgta     1200
agtccaggag ctccatattt taaaaatgct aatcttttag tagctgcaga ttgtacagcc     1260
tatgcttatg gtgactttca caatgatttt ataaagaatc atataacagt aataggatgt     1320
ccaaaacttg atgatgttac atattacaaa gataagttga aagaaattat agaacttaat     1380
gaccttaaga gtataacagt tgttagaatg gaggtacctt gctgttcagg catagtttca     1440
gcagtaaaga ctgctatgct tgaagcaaaa gttatagtac cttttagaga agttattata     1500
ggaactaatg gtgaaattag ataa                                            1524
```

<210> SEQ ID NO 16
<211> LENGTH: 123
<212> TYPE: DNA
<213> ORGANISM: Clostridium acetobutylicum
<220> FEATURE:
<221> NAME/KEY: misc_feature
<223> OTHER INFORMATION: Intergenic region between positions 1014117 and
      1014239 of the C. acetobutylicum ATCC 824 genome

<400> SEQUENCE: 16

```
gtttttctcc caatactttt ttgtgtaaca tatgttactg atatatttat ataattttaa      60
tataatttaa tcataaagac aagtaatttt attttgcgga actttatatt taggaggaaa     120
aaa                                                                   123
```

<210> SEQ ID NO 17
<211> LENGTH: 124
<212> TYPE: DNA
<213> ORGANISM: Artificial
<220> FEATURE:
<223> OTHER INFORMATION: Intergenic region comprising a single
      nucleotide insertion

<400> SEQUENCE: 17

```
gtttttctcc caatactttt ttgtgtaaca tatgttactg atatatttat ataattttaa      60
tataatttaa tcataaagac aagtaatttt attttgcgga actttatatt taggaggaaa     120
aaaa                                                                  124
```

<210> SEQ ID NO 18
<211> LENGTH: 17
<212> TYPE: DNA
<213> ORGANISM: Artificial
<220> FEATURE:
<223> OTHER INFORMATION: Intergenic region forward primer

<400> SEQUENCE: 18

```
gccattaagg aaaaggg                                                    17
```

<210> SEQ ID NO 19
<211> LENGTH: 19
<212> TYPE: DNA
<213> ORGANISM: Artificial
<220> FEATURE:

```
<223> OTHER INFORMATION: Intergenic region reverse primer

<400> SEQUENCE: 19
gctcctggac ttacaagcc                                            19

<210> SEQ ID NO 20
<211> LENGTH: 20
<212> TYPE: DNA
<213> ORGANISM: Artificial
<220> FEATURE:
<223> OTHER INFORMATION: CA_C0884 gene based forward primer

<400> SEQUENCE: 20
gaagagacat aaagccatta                                           20

<210> SEQ ID NO 21
<211> LENGTH: 21
<212> TYPE: DNA
<213> ORGANISM: Artificial
<220> FEATURE:
<223> OTHER INFORMATION: CA_C0884 gene based reverse primer

<400> SEQUENCE: 21
acaataacaa cactagaaga a                                         21

<210> SEQ ID NO 22
<211> LENGTH: 19
<212> TYPE: DNA
<213> ORGANISM: Artificial
<220> FEATURE:
<223> OTHER INFORMATION: CA_C0885 gene based forward primer

<400> SEQUENCE: 22
gctaaaccct gtggatgtc                                            19

<210> SEQ ID NO 23
<211> LENGTH: 22
<212> TYPE: DNA
<213> ORGANISM: Artificial
<220> FEATURE:
<223> OTHER INFORMATION: CA_C0885 gene based reverse primer

<400> SEQUENCE: 23
ggacttacaa gccttaactg aa                                        22

<210> SEQ ID NO 24
<211> LENGTH: 18
<212> TYPE: DNA
<213> ORGANISM: Artificial
<220> FEATURE:
<223> OTHER INFORMATION: CA_C1628 gene based forward primer

<400> SEQUENCE: 24
cccttagagg aggctatg                                             18

<210> SEQ ID NO 25
<211> LENGTH: 18
<212> TYPE: DNA
<213> ORGANISM: Artificial
<220> FEATURE:
<223> OTHER INFORMATION: CA_C1628 gene based reverse primer

<400> SEQUENCE: 25
gccatctctt acatctgg                                             18
```

MICROORGANISM AND METHOD FOR IMPROVED 1,3-PROPANEDIOL PRODUCTION BY FERMENTATION ON A CULTURE MEDIUM WITH HIGH GLYCERINE CONTENT

The present invention relates to a new method and microorganism for the production of 1,3-propanediol from a culture medium with high glycerol content, preferably wherein said glycerol is industrial glycerine. More particularly, the microorganism overexpresses the hcpR and/or frdX genes.

BACKGROUND OF THE INVENTION 1,3-Propanediol (PDO), also called trimethylene glycol or propylene glycol, is one of the oldest known fermentation products. It was originally identified as early as 1881 by August Freund in a glycerol fermented culture containing *Clostridium pasteurianum*. PDO is a typical product of glycerol fermentation, though it has been found in anaerobic conversions of other organic substrates. Very few organisms, all of them bacteria, are able to form PDO. These include enterobacteria of the genera *Klebsiella* (*K. pneumoniae*), *Enterobacter* (*E. agglomerans*) and *Citrobacter* (*C. freundii*), *Lactobacilli* (*L. brevis* and *L. buchneri*) and *Clostridia* (*C. butyricum, C. pasteurianum*). Of these, *C. butyricum* is considered to be the best "natural producer" of PDO in terms of both yield and titer.

PDO, as a bi-functional organic compound, can potentially be used in many different synthesis reactions, including as a monomer for polycondensations to produce polyesters, polyethers and polyurethanes, and in particular, polytrimethylene terephtalate (PTT). Given the structure and reactivity of PDO, it may also be used as a constituent in solvents, adhesives, detergents, cosmetics, textiles (e.g. clothing fibers or flooring) and plastics (e.g. car industry, in packing, or as a coating).

While various chemical methods can be used to produce PDO, they generate waste streams containing extremely polluting substances, thereby preventing chemically produced PDO from being cost competitive with petrochemically available diols, such as 1,2-ethanediol, 1,2-propanediol, and 1,4-butanediol. Although a more environmentally friendly method for the biological conversion of D-glucose to PDO using *Escherichia coli* has been described, this method has several major disadvantages. Notably, culture is discontinuous, due to instability of the producing strain, and further requires the addition of the expensive co-factor vitamin $B_{12}$. Indeed, while PDO can be produced in *E. coli* via a vitamin $B_{12}$-dependent pathway, *E. coli* itself does not produce this co-factor.

Due to the availability of large amounts of industrial glycerine, which comprises glycerol, produced by the biodiesel industry, a continuous, vitamin-$B_{12}$-free process with a higher carbon yield using industrial glycerine as a substrate would be advantageous.

While pure glycerol has a wide variety of applications (e.g. as a food, pharmaceutical, or cosmetic additive), the industrial glycerine produced during biodiesel synthesis generally contains 80-85% of glycerol mixed with salts and water, and therefore requires additional purification steps before it can be used as an additive. As a result, industrial glycerine is treated as a waste product, rather than a valuable commodity, and therefore represents an abundant and inexpensive fermentation substrate for PDO, when compared to other carbon sources, such as glucose or pure glycerol.

*Clostridia* represent very promising strains for the production of PDO. Indeed, *C. butyricum* is able to use pure, but also industrial glycerine, as the sole carbon source for the production of PDO via a $B_{12}$-independent pathway in batch and two-stage continuous fermentation (Papanikolaou et al., 2000). However, at the highest glycerol concentration, the maximal PDO titre obtained was 48.1 g/L at a dilution rate of 0.02 $h^{-1}$, corresponding to a productivity of 0.96 g/L/h. The cultures were conducted with a maximum glycerol concentration in the fed medium of 90 g/L and in the presence of yeast extract, a costly compound containing organic nitrogen that is known to increase bacterial biomass.

WO 2006/128381 discloses the use of industrial glycerine for the production of PDO with batch and fed-batch cultures using "natural producers" of PDO, such as *Klebsiella pneumoniae, C. butyricum* or *C. pasteuricum*. However, the medium used in WO 2006/128381 also contains yeast extract. The maximum productivity reached is also similar to that found by Papanikolaou et al., 2000, comprised between 0.8 and 1.1 g/L/h.

The performance of a recombinant *C. acetobutylicum* strain containing the vitamin $B_{12}$-independent glycerol-dehydratase and the PDO-dehydrogenase from *C. butyricum*, called *C. acetobutylicum* DG1 pSPD5 has been described in Gonzalez-Pajuelo et al., 2005. This strain originally grows and produces PDO in a fed medium containing up to 120 g/L of pure glycerol. In addition, analyses with a fed medium containing 60 g/L of pure or industrial glycerine did not show any differences. These results were also obtained in presence of yeast extract. However, industrial glycerine comprising glycerol concentrations higher than 60 g/L were not tested.

More recently, WO 2010/128070 has disclosed a *C. acetobutylicum* DG1 pSPD5 strain that has been further adapted to grow on a high concentration of industrial glycerine and in the absence of yeast extract. The resulting population of *C. acetobutylicum* DG1 pSPD5 adapted strains was able to produce PDO in culture media containing a relatively high-quality industrial glycerine sourced from Novance (Compiegne, France) with a glycerol concentration of up to 120 g/L with a PDO titer of up to 53.5 g/L, a yield of up to 0.53 g/g and productivity of up to 2.86 g/L/h.

In patent application WO 2012/062832, the inventors described the isolation of clone "c08" from a population of *C. acetobutylicum* DG1 pSPD5 adapted strains obtained by the same process as that described in WO 2010/128070. This clone was able to produce PDO in a culture medium comprising a relatively high-quality industrial glycerine sourced from Novance (Compiègne, France), having a glycerol concentration of approximately 105 g/L. A PDO titer of up to 50.45 g/L, a yield of up to 0.53 g/g and productivity of up to 3.18 g/L/h was observed for the initial population, while the isolated clone c08 showed increased PDO production under the same conditions, with a PDO titer of up to 51.30 g/L, a yield of up to 0.50 g/g and productivity of up to 3.05 g/L/h.

Despite these improvements, there remains a need for increased PDO production (e.g. yield, titer, and/or productivity) from glycerol, in particular from industrial glycerine. There also exists a need for methods and microorganisms producing PDO from industrial glycerine having higher amounts of impurities, which may inhibit PDO production, and/or from industrial glycerine obtained from different origins. Indeed, the composition of industrial glycerine can vary from one manufacturer to another and even between batches. Furthermore, industrial glycerine is increasingly contaminated, having increased levels of impurities called Matter Organic Non-Glycerol (MONG), including fatty acids (e.g. oleic acid, linoleic acid), alcohols, salts and metals, which can inhibit growth and/or PDO production. Finally, there exists a need for methods and microorganisms having a reduced level of residual glycerol. Indeed, reducing residual glycerol levels facilitates downstream PDO purification.

The present invention provides a method and microorganism for the improved production of PDO, in particular from industrial glycerine substrates. Indeed, the inventors have surprisingly found that the overexpression of the hcpR and/or frdX genes, further improves PDO production, as a higher titer of PDO and better yield are observed when compared to the performance of unmodified strains in which the hcpR and/or frdX genes are not overexpressed. In addition, the inventors have surprisingly found that less residual glycerol is present during continuous cultivation. The inventors have also found that strains overexpressing the hcpR and/or frdX genes are able to produce PDO at this improved level in the presence of high concentrations of glycerol contained in industrial glycerine (e.g. up to about 105 g/L), from increasingly impure industrial glycerine, and from industrial glycerine from a variety of origins.

BRIEF DESCRIPTION OF THE INVENTION

The present invention concerns a method for the fermentative production of PDO, comprising culturing a recombinant microorganism converting glycerol into PDO and overexpressing a nitric oxide-responsive transcriptional regulator and/or a ferredoxin-3 like protein, on a medium comprising glycerol. Preferably, the genes coding said proteins are the hcpR and frdX genes, respectively. Preferably, the hcpR and/or frdX gene(s) are overexpressed.

In a preferred embodiment of the method of the invention, the hcpR and/or frdX gene(s) are overexpressed by genetic modification, such as, without any limitation, by mutating the promoter regulating the expression of the hcpR and/or frdX genes, by mutating the intergenic region between the hcpR and frdX genes, by gene duplication, or by overexpressing the hcpR and/or frdX genes from a plasmid.

In a preferred embodiment of the method of the invention, the hcpR and/or frdX genes are overexpressed in the recombinant microorganism by mutating the intergenic region between the two genes, preferably via an insertion, more preferably via an insertion comprising as least one nucleotide, wherein said at least one nucleotide is preferably an 'A' nucleotide. In a particularly preferred embodiment, the intergenic region is mutated by a single base insertion, preferably an 'A' nucleotide. According to a preferred embodiment, said insertion occurs in a region comprising repeated 'A' nucleotides, preferably comprising at least 7 'A' nucleotides. Preferably, the at least one 'A' nucleotide insertion is incorporated between positions 1014234 and 1014240 of the *C. acetobutylicum* ATCC 824 genome (NCBI reference sequence: NC_003030.1).

In a particular embodiment of the method of the invention, the recombinant microorganism is adapted to grow in the presence of a high concentration of glycerol, specifically of industrial glycerine. Preferably, the glycerol concentration in the industrial glycerine is comprised between 90 and 120 g/L, preferably about 105 g/L. Preferably, the industrial glycerine comprises at least 5% fatty acids. The industrial glycerine is preferably a by-product of biodiesel production. Ultimately, PDO is preferably purified.

In a further embodiment of the method of the invention, the recombinant microorganism is a bacterium, preferably selected from species of the genus *Clostridium* or *Klebsiella*, more preferably selected from *Clostridium acetobutylicum, Clostridium butyricum, Clostridium pasteurianum*, and *Klebsiella pneumoniae*.

According to a particular embodiment of the method, the recombinant microorganism is co-cultured with at least one other microorganism in a microbial consortium, preferably with at least one other microorganism of the *Clostridium* genus, more preferably with *Clostridium sporogenes* or *Clostridium sphenoides*, even more preferably with both *Clostridium sporogenes* and *Clostridium sphenoides*.

The present invention also concerns a recombinant microorganism for the production of PDO from glycerol wherein said microorganism converts glycerol into PDO and overexpresses a nitric oxide-responsive transcriptional regulator and/or a ferredoxin-3 like protein. Preferably, in said recombinant microorganism, the genes coding said proteins are the hcpR and frdX genes, respectively. Preferably, the hcpR and/or frdX gene(s) are overexpressed. Preferably, the hcpR and/or frdX gene(s) are overexpressed by genetic modification, such as, without any limitation, by mutating the promoter regulating the expression of the hcpR and/or frdX genes, by mutating the intergenic region between the hcpR and frdX genes, by gene duplication, or by overexpressing the hcpR and/or frdX genes from a plasmid.

In a preferred embodiment, the hcpR and/or frdX genes are overexpressed in the recombinant microorganism by mutating the intergenic region between the two genes, preferably via an insertion, more preferably via an insertion comprising at least one nucleotide, wherein said at least one nucleotide is preferably an 'A' nucleotide. In a particularly preferred embodiment, the intergenic region is mutated by a single base insertion, preferably an 'A' nucleotide. According to a preferred embodiment, said insertion occurs in a region comprising repeated 'A' nucleotides, preferably comprising at least 7 'A' nucleotides. Preferably, the at least one 'A' nucleotide insertion is incorporated between positions 1014234 and 1014240 of the *C. acetobutylicum* ATCC824 genome (NCBI reference sequence: NC_003030.1).

Particularly, the present invention concerns a recombinant microorganism adapted to grow on a culture medium having a high concentration of industrial glycerine, preferably wherein the glycerol concentration in the industrial glycerine is comprised between 90 and 120 g/L. The industrial glycerine may comprise impurities. In one embodiment, the industrial glycerine comprises at least 5% fatty acids.

In a further embodiment, the recombinant microorganism of the invention is a bacterium, preferably selected from species of the genus *Clostridium* or *Klebsiella*, more preferably selected from *Clostridium acetobutylicum, Clostridium butyricum, Clostridium pasteurianum*, and *Klebsiella pneumoniae*. In a particular embodiment, the microorganism of the invention is co-cultured with at least one other microorganism in a microbial consortium, preferably with at least one other microorganism of the *Clostridium* genus, more preferably with *Clostridium sporogenes* or *Clostridium sphenoides*, even more preferably with both *Clostridium sporogenes* and *Clostridium sphenoides*.

The present invention further relates to the recombinant microorganism according to the method described herein.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors that are reported in the publications and that might be used in connection with the invention. Nothing herein is to be construed as an admission that the invention is not entitled to antedate such disclosure by virtue of prior invention.

Furthermore, the practice of the present invention employs, unless otherwise indicated, conventional microbiological and molecular biological techniques within the skill of the art. Such techniques are well known to the skilled worker, and are explained fully in the literature. See, for example, Prescott et al. (1999) and Sambrook et al. (1989) (2001).

It must be noted that as used herein and in the appended claims, the singular forms "a," "an," and "the," include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any material and methods similar or equivalent to those described herein can be used to practice or test the present invention, the preferred material and methods are now described. As used herein, the following terms may be used for interpretation of the claims and specification.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The present invention relates to a new method and microorganism for the fermentative production of PDO.

The term "microorganism" as used herein refers to all types of unicellular organisms, including prokaryotic organisms like bacteria, and eukaryotic organisms like yeasts and fungi, that can generally be found in nature. In the context of the present invention, the microorganism is preferably a bacterium, more preferably selected among the group consisting of Enterobacteriaceae, Bacillaceae, Clostridiaceae, Streptomycetaceae and Corynebacteriaceae. The terms "*Escherichia,*" "*Klebsiella,*" "*Bacillus,*" "*Clostridium,*" "*Clostridia,*" and "*Corynebacterium*" refer to all bacterial species belonging to these families or genera. As a non-limiting example, the bacterial species may be selected among the group consisting of *Escherichia* sp. (preferably *Escherichia coli*), *Klebsiella* sp. (preferably *Klebsiella pneumoniae*), *Bacillus* sp. (preferably *Bacillus subtilis*), *Clostridium* sp. (preferably *Clostridium acetobutylicum*, *Clostridium butyricum*, and *Clostridium pasteurianum*) and *Corynebacterium* sp. (preferably *Corynebacterium glutamicum*).

The term "recombinant microorganism" or "genetically modified microorganism" as used herein refers to a microorganism or a strain of microorganism that has been genetically modified or genetically engineered, for example by adaptation. This means, according to the usual meaning of these terms, that the microorganism of the invention is not found in nature and is genetically modified when compared to a "parental" microorganism, from which it is derived. The "parental" microorganism may occur in nature (i.e. a wild type microorganism) or may have been previously modified, but does not express or over-express the one or more proteins of the present invention (i.e. HcdR and/or FrdX). Accordingly, the recombinant microorganisms of the invention have been modified to express or over-express at least the HcdR and/or FrdX proteins that were not expressed or over-expressed in the parental microorganism.

Preferably, the parental microorganism is selected from the microorganisms listed herein. In a particular embodiment, the parental microorganism is selected from the *Clostridium* species *C. acetobutylicum*, *C. butyricum*, *Clostridium pasteurianum*, and related isolates, or from *Klebsiella* species, such as *K. pneumoniae* and related isolates. More preferably, the parental microorganism is selected from *C. acetobutylicum* strains described in described in Gonzalez-Pajuelo et al., 2005 or in PCT patent application no. WO 2010/128070 or WO 2012/062832. Even more preferably, the parental microorganism is selected from *C. acetobutylicum* DG1 pSPD5 strains, such as the DG1 pSPD5 PD0001VE05 strain.

A variety of genetic modifications may be made to the recombinant microorganism of the invention. As a non-limiting example, endogenous genes can be attenuated, deleted, or over-expressed in the recombinant microorganism, while exogenous genes can be introduced, carried by a plasmid, or integrated into the genome of the strain, for expression within the cell. Such modifications can be performed, for example, by genetic engineering, by adaptation, wherein a microorganism is cultured in that apply a specific stress on the microorganism and induce mutagenesis, or by forcing the development and evolution of new metabolic pathways by combining directed mutagenesis and evolution under specific selection pressure.

In the context of the present invention, the method for the fermentative production of PDO comprises culturing a microorganism converting glycerol into PDO, and overexpressing a nitric oxide-responsive transcriptional regulator and/or a ferredoxin-3 like protein, on a medium comprising glycerol.

The nitric oxide-responsive transcriptional regulator described herein, otherwise known as HcpR, is described in database regprecise.lbl.gov/RegPrecise/ as a transcriptional regulator of the Crp family. It comprises a cAMP binding domain and regulatory subunit of cAMP-dependent protein kinase. It is preferably encoded by the gene CA_C0884 of *C. acetobutylicum*. Exemplary gene and amino acid sequences are shown in SEQ ID NOs: 1 and 2, respectively.

The ferredoxin 3-like protein described herein, otherwise known as FrdX, notably comprises a 4Fe-4S ferredoxin iron-sulfur binding domain. It is preferably encoded by the gene CA_C0885 of *C. acetobutylicum*. Exemplary gene and amino acid sequences are shown in SEQ ID NOs: 3 and 4, respectively.

The nucleotide sequences of the above-mentioned genes, or the amino acid sequences encoded by said genes, are described in Table 1 below, according to their accession number and version in a database and/or according to their sequence identification.

TABLE 1 hcpR and frdX genes and proteins of the invention

| Microorganism | Product name | Strain sequence | NCBI reference sequence and version | Locus tag name | Gene SEQ ID NO | Protein ID | Protein SEQ ID NO |
|---|---|---|---|---|---|---|---|
| *Clostridium acetobutylicum* | cAMP-binding domain-containing protein nitric oxide-responsive transcriptional regulator | ATCC 824 chromosome, complete genome | NC_003030.1 | CA_C0884 | 1 | NP_347520.1 | 2 |
| *Clostridium pasteurianum* | Crp/Fnr family transcriptional regulator | GL11 contig. 1, whole genome shotgun sequence | NZ_MCGV0100000.1 | BEE63_RS05095 | 5 | WP_066020350 | 6 |
| *Clostridium butyricum* | Crp/Fnr family transcriptional regulator | 5521 gcontig_1106103650362, whole genome shotgun sequence | NZ_ABDT01000093.2 | CBY_RS14495 | 7 | WP_003410673.1 | 8 |
| *Clostridium butyricum* | Crp/Fnr family regulator transcriptional regulator | DSM 10702 contig000197, whole genome shotgun sequence | NZ_AQQF01000197.1 | K670_RS19640 | 9 | WP_035765453.1 | 10 |
| *Clostridium butyricum* | Crp/Fnr family transcriptional regulator | NEC8, whole genome shotgun sequence | NC_CBYK010000011.1 | AT697_RS15885 | 11 | WP_046057470.1 | 12 |
| *Clostridium acetobutylicum* | ferredoxin 3-like protein | ATCC 824 chromosome, complete genome | NC_003030.1 | CA_C0885 | 3 | NP_347521.1 | 4 |
| *Clostridium pasteurianum* | Fe—S-binding protein | GL11 contig. 1, whole genome shotgun sequence | NZ_MCGV01000001.1 | BEE63_RS05090 | 13 | WP_066020349.1 | 14 |

The terms "overexpress," "overexpression," and like, as used herein should be taken broadly to include any increase in expression in the corresponding protein, as compared to the expression level protein in an unmodified or "parental" microorganism under the same conditions. It should not be taken to mean that the protein is expressed at any particular level. The term "expression level," as used herein, refers to the amount (e.g. relative amount, concentration) of a protein of interest (or of the gene or mRNA encoding said protein) expressed in a microorganism, which is measurable by methods well-known in the art, such as by qRT-PCR, Western Blot-Immunoblot, Enzyme-linked immunosorbent assay (e.g. ELISA), quantitative proteomic approaches and the like.

A person skilled in the art can easily induce the overexpression of a protein of interest in a microorganism.

As a non-limiting example, one or more endogenous genes, such as the hcpR and/or frdX genes, may be overexpressed by introducing heterologous sequences which favour upregulation in addition to endogenous regulatory elements, or by substituting those endogenous regulatory elements with such heterologous sequences, or by introducing one or more supplementary copies of the endogenous gene chromosomally (i.e. into the chromosome) or extra-chromosomally (e.g. into a plasmid or vector) within the microorganism. In this regard, several copies of a gene can be introduced on a chromosome by methods well-known in the art, such as by genetic recombination. In particular, standard techniques of chromosomal modification may be used in *C. acetobutylicum*, for example according to the method of homologous recombination described in patent application WO 2008/040387 for *Clostridium*. In a preferred embodiment of the invention, a second copy of the gene is introduced in the chromosome (i.e. gene duplication). Alternatively, or in addition, a gene may be introduced into the microorganism on a plasmid or vector, and expressed extra-chromosomally. As a non-limiting example, it may be carried by different types of plasmid that may differ with respect to their origin of replication, depending on the microorganism in which they can replicate, and by their copy number in the cell. For example, a microorganism transformed by a plasmid can contain 1 to 5 copies of the plasmid, about 20 copies, or even up to 500 copies, depending on the nature of the origin of replication of the selected plasmid. A variety of plasmids, which differ in respect of their origin of replication and of their copy number in a cell, are well known in the art and can be easily selected by the skilled practitioner for such purpose. Examples of plasmids which can replicate in *C. acetobutylicum* include, without limitation, the pSOS plasmids (Tummala et al. 1999), plasmids of pSYL series (Lee, 1992), and plasmids of the pMTL series (Chambers et al. 1988), etc.

Another way to overexpress an endogenous gene is to exchange its promoter (i.e. wild-type promoter) with a stronger promoter. Promoters suitable for such purposes may be homologous (originating from the same species) or heterologous (originating from a different species), and are well-known in the art. Indeed, the skilled person can easily select an appropriate promoter for inducing the expression of an endogenous gene, such as the hcpR and/or frdX genes. Promoters that are the most convenient for increasing gene expression level are well-known to the skilled person in the art: these include, among others, promoters Ptrc, Ptac, Plac, and the lambda promoter $P_R$ and $P_L$. These promoters are "inducible" by a particular compound or by specific external conditions such as temperature or light, and/or may be homologous or heterologous. Specific examples of *C. acetobutylicum* promoters leading to high overexpression of genes include the thl, adc, ptb promoters (Tummala et al., 1999).

Endogenous gene expression levels can also be increased by introducing mutations into the coding sequence of a gene or into non-coding sequences. These mutations may be synonymous, when no modification in the corresponding amino acid occurs, or non-synonymous, when the corresponding amino acid is altered. Synonymous mutations do not have any impact on the function of translated proteins, but may have an impact on the regulation of the corresponding genes or even of other genes, if the mutated sequence is located in a binding site for a regulator factor. Non-synonymous mutations may have an impact on the function of the translated protein as well as on regulation depending the nature of the mutated sequence.

In particular, mutations in non-coding sequences may be located upstream of the coding sequence (i.e. in the promoter region, in an enhancer, silencer, or insulator region, in a specific transcription factor binding site) or downstream of the coding sequence. Mutations introduced in the promoter region may be in the core promoter, proximal promoter or distal promoter. Mutations may be introduced by site-directed mutagenesis using, for example, Polymerase Chain Reaction (PCR), by random mutagenesis techniques for example via mutagenic agents (Ultra-Violet rays or chemical agents like nitrosoguanidine (NTG) or ethylmethanesulfonate (EMS)) or DNA shuffling or error-prone PCR or using culture conditions that apply a specific stress on the microorganism and induce mutagenesis. The insertion of one or more supplementary nucleotide in the region located upstream of a gene can notably modulate gene expression. As a non-limiting example, one or more mutations may be introduced into the intergenic region located between the hcpR and/or frdX genes (the full sequence comprising the hcpR and frdX genes and the parental intergenic region is shown in the sequence of SEQ ID NO: 15, while the parental sequence of the intergenic region alone is shown in the sequence of SEQ ID NO: 16). As a non-limiting example, the insertion of an "A" nucleotide may be introduced in the intergenic region. An example of such an insertion is shown in the sequence of SEQ ID NO: 17.

In the context of the present invention, the recombinant microorganism preferably overexpresses the hcpR and/or frdX gene(s). Preferably, the hcpR and/or frdX gene(s) are overexpressed by at least 1.5-fold, more preferably by at least about 2-fold, even more preferably by at least 3-fold or by about 4-fold.

According to a first preferred embodiment, the hcpR and/or frdX gene(s) are overexpressed by mutating the intergenic region between the two genes, preferably via an insertion. Preferably, said intergenic mutation modifies the promoter region regulating the expression of the hcpR and/or frdX gene(s), inducing overexpression. Preferably, said intergenic mutation induces the overexpression of both the hcpR and frdX genes. Indeed, the hcpR and frdX genes are arranged as a bi-directional gene pair in *C. acetobutylicum*. However, according to the type of intergenic mutation, only one of the hcpR and frdX genes may be overexpressed. Preferably, said intergenic mutation is comprised between positions 1014117 and 1014239 of the *C. acetobutylicum* ATCC 824 genome.

Preferably, the intergenic region is mutated by the insertion of at least one nucleotide selected from the 'A,' 'C,' 'T,' and 'G' nucleotides. Preferably, the intergenic region is mutated by the insertion of at least one 'A' nucleotide, more preferably one 'A' nucleotide. Preferably, the at least one nucleotide is inserted into a region wherein a same nucleotide is repeated at least two, three, four, five, six, seven or more times (e.g. insertion of an 'A' nucleotide in a nucleotide stretch comprising 'AAAAAA'). When said insertion is an 'A' nucleotide, said insertion may be further located at position 1014240 of the *C. acetobutylicum* ATCC 824 genome. Preferably, said at least one 'A' is incorporated between positions 1014234 and 1014240 of the *C. acetobutylicum* ATCC 824 genome.

According to a second preferred embodiment, the hcpR and/or frdX gene(s) is/are overexpressed by introduction of said gene(s) into the microorganism on an exogenous vector or plasmid, more preferably under the control of an inducible promoter.

According to a third preferred embodiment, the hcpR and/or frdX gene(s) is/are overexpressed by introduction of at least one additional copy of said gene in the chromosome (i.e. gene duplication).

In view of the gene and amino acid sequences provided herein, and using the information available in databases such as UniProt (for proteins), GenBank (for genes), or NCBI (for proteins or genes), the skilled practitioner can easily determine the sequence of a specific protein and/or gene of a microorganism, and identify equivalent proteins or genes, or homologs thereof, in other microorganisms. This routine work can be performed for example by alignment of a specific gene (or protein) sequence of a microorganism with gene (or protein) sequences or the genome (or proteome) of other microorganisms, which can be found in the above-mentioned databases. Such sequence alignment can advantageously be performed using the BLAST algorithm developed by Altschul et al. (1990). Once sequence homology has been established between sequences, a consensus sequence can be derived and used to design degenerate probes in order to clone the corresponding homolog gene (and hence homolog protein) of the related microorganism. These routine methods of molecular biology are well-known to the person skilled in the art.

It shall be further understood that, in the context of the present invention, should an exogenous gene encoding a protein of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described by Graf et al. (2000), Deml et al. (2001) and Davis & Olsen (2011). Several software programs have notably been developed for codon optimization determination such as the GeneOptimizer® software (Lifetechnologies) or the OptimumGene™ software of (GenScript). In other words, the exogenous gene encoding a protein of interest is preferably codon-optimized for expression in a specific microorganism.

In the context of the method and microorganism of the invention, the recombinant microorganism may comprise additional modifications with regards to the parent strain. As a non-limiting example, the recombinant microorganism may have been previously adapted for increased PDO production from a culture medium comprising glycerol. Methods for directing the glycerol metabolism towards production of PDO are known in the art (see for instance WO 2006/128381, González-Pajuelo & al. 2006).

In a preferred embodiment, if the recombinant microorganism is *C. acetobutylicum*, it has preferably been previously adapted, more preferably by an anaerobic continuous process, for growth and production of PDO from a culture medium with high glycerol content, presenting an increased flux of PDO production. The adaptation of the strain *C. acetobutylicum* is preferably carried out by an anaerobic continuous process, which is a technique well known by the skilled person. Among the particulars of this process known by the one skilled in the art, it may be for example mentioned that fed medium is added to the fermenter continuously and an equivalent amount of converted nutrient solution with microorganisms is simultaneously removed from the system. The rate of nutrient exchange is expressed as the dilution rate. Hence the dilution rate is applied to the culture medium, takes into consideration maximum growth rate of the microorganism and impacts the rate of intake and withdrawal of the medium.

The *C. acetobutylicum* strain may be adapted by introducing extra copies of the PDO operon from *C. butyricum*, encoding enzymes involved in the vitamin $B_{12}$-independent PDO pathway. In particular, the PDO operon from *C. butyricum* may be overexpressed by either a plasmid or integrated into the chromosome of the strain *C. acetobutylicum* to be adapted. For example, the pSPD5 plasmid can be used for overexpression of the PDO operon in *C. acetobutylicum* (Gonzalez-Pajuelo et al., 2006).

Alternatively or in addition, said recombinant microorganism may be adapted to grow in a culture medium having a high glycerol content, specifically a high concentration of glycerol originating from industrial glycerine, by a selection pressure culturing process as disclosed in WO 2010/128070 (see in particular page 7, line 10 to page 8, line 23 and Examples 2, 3, and 4).

Strains of *C. acetobutylicum* that have been genetically modified for the production of PDO from glycerol as a sole source of carbon are known in the art and disclosed, particularly, in applications WO 2001/04324 and WO 2010/128070. Finally, the *C. acetobutylicum* strain may be previously adapted by the process described in WO 2012/062832.

As a non-limiting example, the strain *C. acetobutylicum* to be adapted may be cultivated in continuous culture using a fed medium containing between 90 and 120 g/L of glycerol and preferably of about 105 g/L of raw glycerol. Said "adaptation" of the producing microorganism is obtained by culturing the microorganism on a culture medium comprising high industrial glycerine content at a low dilution rate, and selecting the adapted microorganism able to grow on the culture medium having high concentration of glycerol originating from industrial glycerine. A dilution rate between 0.005 and 0.02 $h^{-1}$ corresponds to a "low dilution rate" while a dilution rate between 0.02 and 0.1 $h^{-1}$ corresponds to common dilution rates. As a non-limiting example, the strain *C. acetobutylicum* to be adapted may be cultivated at a low dilution rate over a period ranging from 24 hours to 10 days, preferably more than 2 days, more preferably about 8 days. The dilution rate is generally comprised between 0.005 and 0.1 $h^{-1}$, preferably between 0.005 and 0.02 $h^{-1}$. The dilution rate can be changed during the adaptation method, eventually with a first step comprised between 0.005 and 0.02 $h^{-1}$ and a second step where the dilution rate is increased up to 0.1 $h^{-1}$, more preferably up to 0.06 $h^{-1}$, even more preferably up to 0.07 $h^{-1}$.

In a specific embodiment of the invention, the strain *C. acetobutylicum* to be adapted is cultivated in continuous culture using a fed medium containing between 90 and 120 g/L of glycerol and preferably of about 105 g/L of raw glycerol, at a low dilution rate comprised between 0.005 and 0.02 $h^{-1}$, preferably 0.02 $h^{-1}$. Over a period of up to 10 days, preferably between 5 and 8 days, the strain *C. acetobutylicum* is adapted to the high glycerine concentration present in the fed medium, and the dilution rate can be increased up to 0.1 $h^{-1}$, preferably up to 0.07 $h^{-1}$.

The "culture medium" refers to a culture medium appropriate for the growth and the diol-production of the recombinant microorganism, wherein said culture medium comprises glycerol, which may or may not be the sole carbon source present in the culture medium. The culture medium may or may not comprise an organic nitrogen source. Nitrogen is a naturally occurring element that is essential for growth and reproduction in both plants and animals. It is found in amino acids and in many other organic and inorganic compounds. "Organic nitrogen" means, according to the invention, a nitrogen comprising organic compound obtained from living organisms. Usual sources of organic nitrogen for bacterial culture comprise yeast extract.

Glycerol may be the sole carbon source present in the culture medium. Alternatively, one or more additional carbon sources (e.g. glucose) may be present in the culture medium. The glycerol present in the culture medium may be pure or industrial glycerine.

Preferably, the culture medium does not comprise yeast extract. Even more preferably, the culture medium does not comprise any organic nitrogen source. Preferably, glycerol is the sole carbon source present in the culture medium.

The term "glycerol" may be used interchangeably herein with the term "glycerine," and may comprise pure and/or industrial glycerine. Industrial glycerine may be obtained as a bioproduct from biodiesel production, (e.g. from the transesterification of glycerides with short-chain alcohols). Alternatively, industrial glycerine may be obtained from plant or animal oils and fats, for example by saponification, transesterification and/or hydrolysis reactions.

"Pure glycerol" refers to a glycerol product having a purity of greater than 95% by weight, of glycerol. In some cases, pure glycerol may have a purity of greater than 97%, even more of greater than 99% or 99.2%. The remainder of the glycerol product is preferably composed of water (e.g. about 3 to 5% by weight). Pure glycerol has very few remaining impurities. Pure glycerol may notably be obtained by purification using one or more processes, such as distillation.

"Industrial glycerine" refers to a glycerol product obtained from an industrial process without substantial purification. Industrial glycerine can also be designated as "raw glycerine," "raw glycerol," "crude glycerol," or "industrial glycerol." Industrial glycerine generally comprises from 5 to 95% by weight of glycerol, in particular from 40 to 90% by weight of glycerol, more particularly from 60 to 90% by weight of glycerol, even more particularly from about 65 to 85% by weight of glycerol or about 70% to 85% by weight of glycerol. The remaining fraction of industrial glycerine may comprise water also referred to as moisture, mineral salts, and Matter Organic Non-Glycerol (MONG), which comprises other non-glycerol organic compounds and glycerides. In particular, industrial glycerine further comprises impurities, such as alcohol (e.g. methanol), mineral salts, unreacted mono-, di-, and tri-acylglycerols, methyl esters and one or more fatty acids (e.g. palmitic acid, stearic acid, oleic acid, linolenic acid, linoleic acid and arachidic acid).

According to a preferred embodiment, industrial glycerine preferably contains more than about 60%, 70% or 80% by weight of glycerol and less than about 15% by weight of water and impurities. According to a preferred embodiment, the concentration of mineral salts is less than 10%, preferably less than 5%. According to a preferred embodiment, the concentration of fatty acids comprised in the MONG, in certificates of analysis, is less than 20%, preferably less than 10%, even more preferably less than 5%. According to an alternative preferred embodiment, the concentration of fatty acids or MONG is preferably at least 5%, more preferably at least 10%, even more preferably comprised between 5 and 10%.

Industrial processes from which industrial glycerine is obtained as a by-product are, inter alia, manufacturing methods where fats and oils, particularly fats and oils of plant or animal origin, are processed into industrial products such as detergent or lubricants. In such manufacturing methods, industrial glycerine is considered as a by-product. The exact composition of industrial glycerine will depend on the initial glycerol source (e.g. animal fat or plant oil, such as sunflower oil, canola oil, soybean oil, mustard seed, etc.), and the method and conditions used in glycerol extraction and downstream treatment, for example, in biodiesel production.

In a particular embodiment, the industrial glycerine is a by-product from biodiesel production. Preferably, the industrial glycerine comprises known impurities of glycerol obtained from biodiesel production, comprising about 80 to 85% of glycerol with salts, water and some other organic compounds (i.e. MONG), comprising compounds such as fatty acids, such as those as listed above. Industrial glycerine obtained from biodiesel production has not been subjected to further purification steps.

The terms "high glycerol content" or "high glycerol concentration" as used herein refers to glycerol concentrations equal or superior to 90 g/l of glycerol in the culture medium. In preferred embodiments, the culture medium comprises glycerol at a concentration comprised between 90 and 120 g/L, preferably comprised between 105 and 110 g/L, more preferably about 105 g/L or 109 g/L.

In some cases, PDO production may be further increased and/or residual glycerol levels further decreased by co-culturing the recombinant microorganism in the presence of at least one other microorganism, in a so-called microbial consortium. The terms "microbial consortium" or "co-culture" are used interchangeably to denote the use of two or more microbial species in the fermentation process. Preferably, the one or more additional strains used in co-culture do not ferment glycerol or produce PDO.

As a non-limiting example, the microbial consortium may comprise at least two *Clostridium* strains, such as one *C. acetobutylicum* strain and at least one strain chosen among strains of the *Clostridium* genus, such as strains of *C. sporogenes* and/or strains of *C. sphenoides*. As a further example, the microbial consortium may comprise at least three *Clostridium* strains, such as at least one *C. acetobutylicum* strain, at least one *C. sporogenes* and at least one strain of *C. sphenoides*. In either of the cases described above, the majority of the microbial consortium may belong to the *C. acetobutylicum* species. For example, the microbial consortium may comprise more than 85% of *C. acetobutylicum*, from 0.001% to 0.2% of *C. sporogenes* and/or from 0.1% to 15% of *C. sphenoides*, considering that the totality of the cells contained in the culture corresponds to 100%. In particular, the microbial consortium may comprise from 85% to 99.8% of *C. acetobutylicum*, from 0.001% to 0.15% of *C. sporogenes* and/or from 0.2% to 15% of *C. sphenoides*, or from 90% to 99.8% of *C. acetobutylicum*, from 0.002% to 0.13% of *C. sporogenes* and/or from 0.2% to 10% of *C. sphenoides*.

Thus, in a preferred embodiment, the microorganism of the present invention is co-cultured in a microbial consortium. Said microbial consortium preferably comprises the recombinant microorganism disclosed herein, or as described in the method of the invention disclosed herein, in co-culture with at least one, preferably two, other microorganisms. According to a particularly preferred embodiment, the recombinant microorganism is co-cultured with at least one strain of *C. sphenoides*, more preferably with at least one strain of *C. sphenoides* and at least one strain of *C. sporogenes*. Preferably, the recombinant microorganism of the invention is a *C. acetobutylicum* strain, even more preferably adapted for growth and production of PDO from a culture medium with high glycerol content and specifically with a high concentration of glycerol contained in industrial glycerine.

In a preferred embodiment, the microbial consortium of the invention comprises more than 85% of *C. acetobutylicum*, from 0.001% to 0.2% of *C. sporogenes* and/or from 0.1% to 15% of *C. sphenoides*, considering that the totality of the cells contained in the culture corresponds to 100%. In a more preferred embodiment, the microbial consortium comprises from 85% to 99.8% of *C. acetobutylicum*, from 0.001% to 0.15% of *C. sporogenes* and/or from 0.2% to 15% of *C. sphenoides*. In an even more preferred embodiment, the microbial consortium comprises from 90% to 99.8% of *C. acetobutylicum*, from 0.002% to 0.13% of *C. sporogenes* and/or from 0.2% to 10% of *C. sphenoides*.

In the method of the present invention, the production of PDO is preferably carried out by an anaerobic continuous fermentation by culturing the recombinant microorganism, or microbial consortium of the invention described above in a culture medium comprising glycerol as the sole source of carbon, said culture medium being a minimal medium without addition of organic nitrogen.

The term "minimal medium" means a culture medium strictly mineral comprising a chemically defined composition on which organisms are grown apart from the glycerine solution. Such culture media are disclosed in the art, particularly in WO 2010/128070 and WO 2011/042434, the contents of which are incorporated herein by reference in their entirety.

In a preferred embodiment, the PDO thus obtained from the method according to the invention is further purified. Methods for recovering and eventually purifying PDO from a fermentation medium are known to the skilled person. PDO may be isolated by distillation. In most embodiments, PDO is distilled from the fermentation medium with a by-product, such as acetate, and then further purified by known methods. A particularly preferred purification method is disclosed in applications WO 2009/068110 and WO 2010/037843, the content of which are incorporated herein by reference in their entirety.

Continuous fermentation processes are known to the person skilled in the art. The fermentation process is generally conducted in reactors with an inorganic culture medium of known defined composition adapted to the bacteria used, containing at least industrial glycerine, a by-product from biodiesel production, and if necessary a co-substrate for the production of the metabolite.

This method of the invention is preferably realized in a continuous process. The person skilled in the art is able to manage each of these experimental conditions, and to define the culture conditions for the microorganisms according to the invention according to his general knowledge. In particular clostridia are fermented at a temperature between 20° C. and 60° C., preferentially between 25° C. and 40° C. for *C. acetobutylicum*.

In a specific embodiment of the invention, the strain *C. acetobutylicum* DG1 pSPD5 Type 130P or Type 008P is cultivated in continuous culture using a fed medium containing approximately 105 g/L or 109 g/L of raw glycerol, at a dilution rate comprised between 0.035 and 0.08 $h^{-1}$, preferably 0.07 h$^{-1}$ (see examples 1 and 2). Said method, in its different embodiments, leads to production of PDO of at least 52 g/L, with a yield comprised between 0.4 and 0.6 g/g and a productivity superior to 2.9 g/L/h for a dilution rate of 0.7 h$^{-1}$. Preferably, the yield is comprised between 0.4 and 0.5 g/g and the productivity is superior to 3.6 g/L/h, even more preferably superior to 3.65 g/L/h. The method of the invention, in certain embodiments, further leads to a residual glycerol level of less than 3.7 g/L. Preferably, the residual glycerol level is approximately 3.6 g/L.

FIGURES

FIG. 1: Obtention of *Clostridium acetobutylicum* DG1 pSPD5 Type 130P strain by adaptation of the Type 008P strain on raw glycerine. Dynamic of $OD_{620nm}$ (OD units or ODU, squares), residual glycerol (g/L; hatches), PDO concentration (g/L; triangles) and feed flow rate (mL/h; circles) of the continuous culture are shown as a function of culture duration (days; d).

Figure 2:
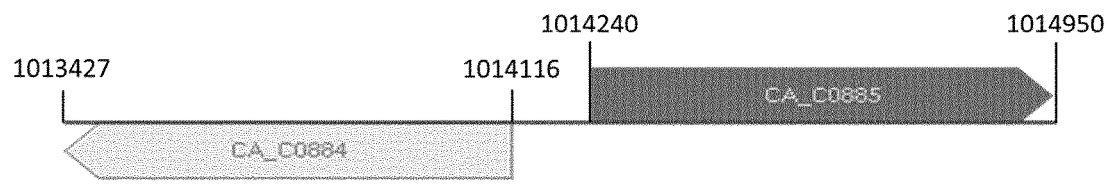

FIG. 2: Chromosomal organization of the hcpR and frdX genes in *C. acetobutylicum*. The genes hcpR and frdX are organized as a bi-directional gene pair, with a 123 bp intergenic region located between the two genes. Nucleotide positions within the *C. acetobutylicum* ATCC 824 genome (NCBI reference sequence: NC_003030.1) are indicated.

Figure 3:
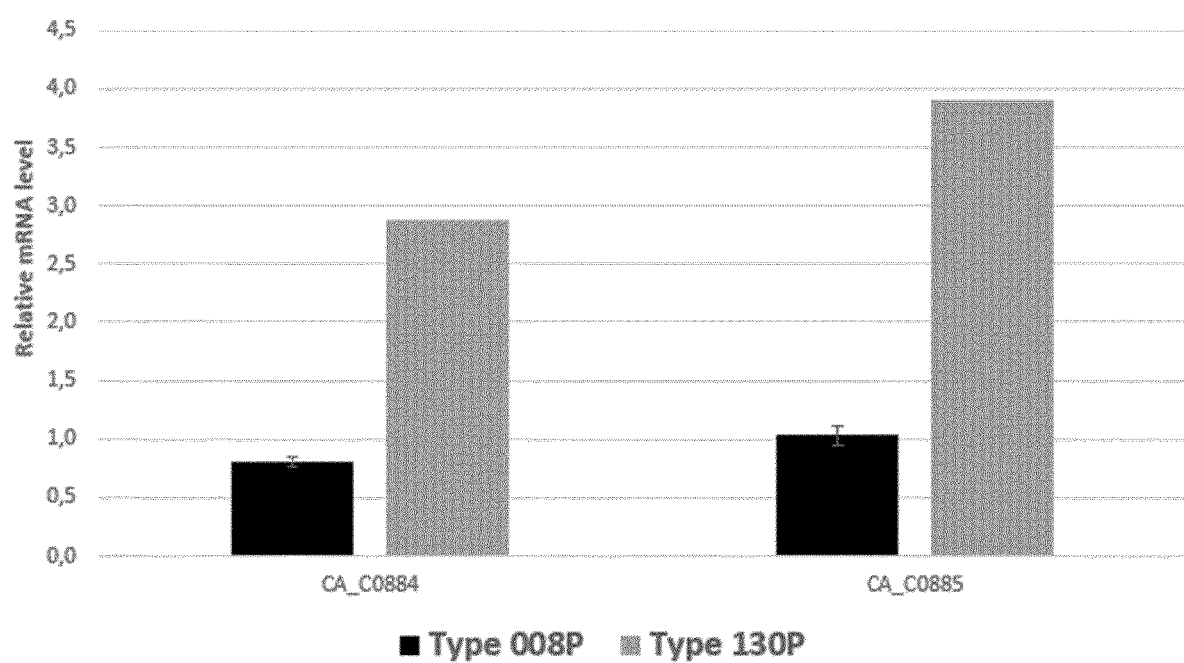

FIG. 3: Overexpression of the hcpR and frdX genes by quantitative PCR. Both hcpR and frdX were overexpressed in the 130P strain, as compared to the parent strain Type 008P, as determined by qRT-PCR. Black bars: Type 008P; Grey bars: Type 130P.

EXAMPLES

The present invention is further defined in the following examples. It should be understood that these example, while indicating preferred embodiments of the invention, are given by way of illustration only. From above disclosure and these examples, the person skilled in the art can make various changes of the invention to adapt it to various uses and conditions without modifying the essential means of the invention.

Example 1

Continuous Culture of *Clostridium acetobutylicum* DG1 (pSPD5) on Raw Industrial Glycerol and Obtention of the Microorganism Type 130P Bacterial Strains:
Type 008P: *C. acetobutylicum* strain DG1 pSPD5 adapted on high concentrations of raw glycerine as described in patent application WO 2010/128070
Type 130P: *C. acetobutylicum* strain DG1 pSPD5 Type issued from a continuous culture form *C. acetobutylicum* strain DG1 pSPD5 Type 008P on high concentrations of raw industrial glycerine, and overexpressing the hcpR and frdX genes, as described herein The synthetic media used for clostridia batch cultivations contained, per liter of tap water: glycerol, 30 g; $KH_2PO_4$, 0.5 g; $K_2HPO_4$, 0.5 g; $MgSO_4$, $7H_2O$, 0.2 g; $CoCl_2$ $6H_2O$, 0.01 g; $H_2SO_4$, 0.1 ml; $NH_4Cl$, 1.5 g; biotin, 0.16 mg; p-amino benzoic acid, 32 mg; $FeSO_4$, $7H_2O$, 0.028 g. The pH of the medium was adjusted to 6.3 with $NH_4OH$ 3N. Commercial glycerol purchased from SDS Carlo_Erba (purity 99%) was used for batch cultivation. The feed medium for continuous cultures contained, per liter of tap water: glycerol from raw glycerine, 105 g; $KH_2PO_4$, 0.50 g; $K_2HPO_4$, 0.50 g; $MgSO_4$, $7H_2O$, 0.2 g; $NH_4Cl$, 1.5 g; $CoCl_2$ $6H_2O$, 0.026 g; biotin, 0.16 mg; p-amino benzoic acid, 32 mg; $FeSO_4$, $7H_2O$, 0.04 g; anti-foam, 0.05 ml; $ZnSO_4$, $7H_2O$, 8 mg; $CuCl_2$, $2H_2O$, 4 mg; $MnSO_4$, $H_2O$, 0.04 g; $H_3BO_3$, 2 mg; $Na_2MoO_4$, $2H_2O$, 0.8 mg. Medium pH was adjusted between 3.5 and 4 with $H_2SO_4$ 96%.

Raw glycerine, from the transesterification process for biodiesel, was provided by two different providers and had the following composition:
from ADM (Rolle, Switzerland) (using vegetable oil; purity 80.9%; Moisture 12.6%; MONG 0.39%; Ash 6.2%),
from Greenergy (London, UK) (using cooking oil; purity 76.5%; Moisture 10.2%; MONG 7.1%; Ash 6.3%).

Optionally, these glycerines were pretreated by acidification.

The purity and MONG composition has an incidence on the toxicity of the glycerine on the microorganism. The Greenergy (London, UK) glycerine is both less pure and more dirty, therefore more toxic for the microorganism, than the ADM (Rolle, Switzerland) glycerine, because of the high concentration of MONG. Indeed, MONG concentration in the Greenergy (London, UK) glycerine is above 5%.

The following example shows the adaptation of the strain Type 008P on coarser glycerine (from ADM to Greenergy) to get a new strain named Type 130P, that is able to grow and produce PDO on less refined industrial glycerine. This adaptation is highly advantageous, as less refined industrial glycerine is a cheaper raw material for the fermentation process.

Experimental Set-Up:
Continuous cultures were performed in a 5 l Tryton bioreactor (Pierre Guerin, France) with a working volume of 2000 ml. The culture volume was kept constant at 2000 ml by automatic regulation of the culture level. Cultures were stirred at 200 RPM, the temperature was set to 35° C. and pH was maintained constant at 6.5 by automatic addition of $NH_4OH$ 5.5N. To create anaerobic conditions, the sterilized medium in the vessel was flushed with sterile $O_2$-free nitrogen for one hour at 60° C. and flushed again until 35° C. was attained (flushing during 2 hours). The bioreactor gas outlet was protected from oxygen by a pyrogallol arrangement (Vasconcelos et al, 1994). After sterilization, the feed medium was also flushed with sterile $O_2$-free nitrogen until room temperature was reached and kept under nitrogen to avoid $O_2$ entry.

Analytical Procedures:
Cell concentration was measured turbidimetrically at 620 nm ($OD_{620nm}$) and correlated with cell dry weight, which was determined directly. Glycerol, PDO, ethanol, lactate, acetic and butyric acid concentrations were determined by HPLC analysis. Separation was performed on a Biorad Aminex HPX-87H column and detection was achieved by refractive index. Operating conditions were as follows: mobile phase sulphuric acid 0.5 mM; flow rate 0.5 ml/min, temperature, 25° C.

Batch and Continuous Cultures Process and Results:
A culture growing in a 100 ml flask on synthetic medium (the same as described above for batch culture but with the addition of acetic acid, 2.2 g/L and MOPS, 23.03 g/L) taken at the end of exponential growth phase was used as inoculum (5% v/v).

Cultures were first grown in batch mode. At the early exponential growth phase, we performed a pulse of glycerol with the feed medium (the same as described for feed culture). Glycerol from raw glycerine was added at a static flow rate during 3 hours (i.e. an addition of 18 g/L of glycerol). Then, the growth continued in batch mode and before the end of the exponential growth phase the continuous feeding started with a dilution rate of 0.035 h$^{-1}$ of feed medium containing 105 g/L of glycerol from raw glycerine provided by ADM (Rolle, Switzerland) only. As can be seen in FIG. 1, after 3 days with a dilution rate of 0.035 h$^{-1}$, glycerol accumulation started and reached 46.6 g/L at 6.5 residence times (RT, calculated according to the formula shown below), corresponding to the first peak of residual glycerine. This accumulation was coupled with a decrease of PDO production (up to 31 g/L instead of 52 g/L) and biomass production (1.8 ODU instead of 5.6 ODU). This accumulation was followed by a quick re-consumption, after 9 RT at a dilution rate of D=0.035 h$^{-1}$ residual glycerol was drop down at 2.9 g/L. At this time (12 days after the inoculation), the dilution rate was increased from 0.035 h$^{-1}$ to 0.070 h$^{-1}$ in five days. After 9 RT at a dilution rate of D=0.07 h$^{-1}$, performances stabilized at 5.5±1.1 g/L of glycerol and 51.6±0.7 g/L of PDO.

After this stabilization, (28 days after the inoculation (see FIG. 1), raw glycerine of the feed was changed to a blend of raw glycerine provided by ADM (50%; Rolle, Switzerland) and by Greenergy (50%; London, UK), thereby increasing the level of MONG, and glycerine toxicity for microorganisms.

This modification of the feed composition induced cycles of glycerol accumulation (max at 35.1 g/L) and drops of PDO production (min at 37.4 g/L) during 13 days. The culture was monitored for stabilization via the key factors (OD, residual glycerol and PDO concentration), and the new adapted strain 130P was identified for storage at day 45 (see FIG. 1).

At this step, the new strain was sequenced and compared to the sequence of 008P. We identified the intergenic mutation described in Example 3 below.
Performances of the resulting strain Type 130P are presented below in Table 2.
Formula for the Calculation of Residence Time from Dilution Rate $$RT = \frac{1}{DR}$$

RT: residence time (h)

DR: dilution rate (h$^{-1}$)

TABLE 2

Performances of the *C. acetobutylicum* DG1 pSPD5 strain type 130P. The feed medium contained 105 g/L of glycerol from raw glycerine provided by ADM (Rolle, Switzerland) and Greenergy (London, UK) at a dilution rate of 0.070 h$^{-1}$.

| | PDO Production performances Type 130P strain |
|---|---|
| Feed glycerol (ADM/Greenergy) (g.l$^{-1}$) | 109 |
| PDO (g.l$^{-1}$) | 52.0 |
| YPDO (g.g$^{-1}$) | 0.48 |
| QPDO (g.l$^{-1}$.h$^{-1}$) | 3.62 |
| Dilution rate (h$^{-1}$) | 0.070 |
| Residual glycerol (g.l$^{-1}$) | 7.50 |

TABLE 2-continued

Performances of the *C. acetobutylicum* DG1 pSPD5 strain type 130P. The feed medium contained 105 g/L of glycerol from raw glycerine provided by ADM (Rolle, Switzerland) and Greenergy (London, UK) at a dilution rate of 0.070 h$^{-1}$.

| | PDO Production performances Type 130P strain |
|---|---|
| Biomass (g.l$^{-1}$) | 1.4 |
| Acetic acid (g.l$^{-1}$) | 5.1 |

YPDO: PDO yield (g/g of glycerol engaged)
QPDO: PDO volumetric productivity

Example 2

PDO Production Performances of *C. acetobutylicum* DG1 pSPD5 Strains Type 008P and 130P in a Chemostat by Continuous Culture with High Concentration of Raw Glycerine The synthetic media used for clostridia batch cultivations contained per liter of tap water: glycerol, 30 g; $KH_2PO_4$, 0.5 g; $K_2HPO_4$, 0.5 g; $MgSO_4$, $7H_2O$, 0.2 g; $CoCl_2$, $6H_2O$, 0.01 g; $H_2SO_4$, 0.1 ml; $NH_4Cl$, 1.5 g; biotin, 0.16 mg; p-amino benzoic acid, 32 mg and $FeSO_4$, $7H_2O$, 0.028 g. The pH of the medium was adjusted to 6.3 with $NH_4OH$ 3N. Commercial glycerol purchased from SDS Carlo_Erba (purity 99%) was used for batch cultivation. The feed medium for continuous cultures contained per liter of tap water: glycerol from raw glycerine, 105 g; $KH_2PO_4$, 0.50 g; $K_2HPO_4$, 0.50 g; $MgSO_4$, $7H_2O$, 0.2 g; $NH_4Cl$, between 0 to 1.5 g; $CoCl_2$ $6H_2O$, between 0.013 to 0.026 g; biotin, between 0.08 to 0.16 mg; p-amino benzoic acid, between 16 to 32 mg; $FeSO_4$, $7H_2O$, 0.04 g; anti-foam, 0.05 ml; $ZnSO_4$, $7H_2O$, 8 mg; $CuCl_2$, $2H_2O$, 4 mg; $MnSO_4$, $H_2O$, 0.02 g to 0.04 g; $H_3BO_3$ between 0 to 2 mg; $Na_2MoO_4$, $2H_2O$, between 0 to 0.8 mg. Medium pH was adjusted between 3.5 and 4 with $H_2SO_4$ 96%.

Raw glycerine, from the transesterification process for biodiesel, was obtained from several different sources and had the following composition:

Novance (Compiegne, France) (using vegetable oil; purity between 82 to 85%; Moisture between 8 to 13%; MONG between 0.1 to 0.3%; Ash 1.4%)

ADM (Rolle, Switzerland) (using vegetable oil; purity 80.9%; Moisture 12.6%; MONG 0.39%; Ash 6.2%), used in a blend with Greenergy glycerine Greenergy (London, UK) (using cooking oil; purity 76.5%; Moisture 10.2%; MONG 7.1%; Ash 6.3%), used in a blend with ADM glycerine Optionally, these glycerine were pretreated by acidification.

As explained above in Example 1, the purity and MONG composition has an incidence on the toxicity of the glycerine on the microorganism.

Experimental set-up is as described in Example 1, above.
Batch and Continuous Cultures Process:

A culture growing in a 100 ml flask on synthetic medium (the same as described above for batch culture but with addition of acetic acid, 2.2 g/L and MOPS, 23.03 g/L) taken at the end of exponential growth phase was used as inoculum (5% v/v).

Cultures were first grown in batch mode. At the early exponential growth phase we performed a pulse of glycerol with the feed medium (the same as described for feed culture). Glycerol from raw glycerine was added at a static flow rate during 3 hours (i.e. an addition of 18 g/L of glycerol). Then, the growth continued in batch mode and before the end of the exponential growth phase the continuous feeding started with a dilution rate of 0.035 $h^{-1}$. Five to eight days after inoculation of the bioreactor, the dilution rate was increased from 0.035 $h^{-1}$ to 0.070 $h^{-1}$ in five days. After that, stabilization of the culture was followed by PDO production and glycerol consumption using the HPLC protocol described in example 1 in Analytical procedures.

TABLE 3

Performances of the *C. acetobutylium* Type 008P and of the Type 130P strains in continous culture. The feed medium contained 105 g/L of glycerol from raw glycerine at dilution of 0.070 $h^{-1}$. Mean data from respectively 8 and 17 chemostats. Providers of glycerine used in the cultures are indicated for each strain. Novance (Compiègne, France) corresponds to a relatively clean and pure glycerine while ADM (Rolle, Switzerland) and Greenergy (London, UK) provide glycerine that is less pure with more contaminants, and therefore more toxic to the microorganism.

|  | Type 008P strain Raw glycerine used: Novance | Type 008P strain Raw glycerine used: ADM/ Greenergy blend | Type 130P strain Raw glycerine used: Novance or ADM/ Greenergy blend* |
|---|---|---|---|
| Feed glycerol (g.l$^{-1}$) | 105 | 104 | 106 |
| 1,3-propanediol (g.l$^{-1}$) | 49.8 | 41.7 | 52.3 |
| YPDO (g.g$^{-1}$) | 0.47 | 0.40 | 0.49 |
| QPDO (g.l$^{-1}$.h$^{-1}$) | 3.55 | 2.90 | 3.70 |
| Dilution rate (h$^{-1}$) | 0.072 | 0.070 | 0.071 |
| Residual glycerol (g.l$^{-1}$) | 5.7 | 18.6 | 3.6 |
| Biomass (g.l$^{-1}$) | 2.3 | 1.7 | 2.3 |
| Acetic acid (g.l$^{-1}$) | 2.5 | 2.8 | 3.1 |
| Butyric acid (g.l$^{-1}$) | 10.8 | 8.2 | 10.6 |

YPDO: PDO yield (g/g of glycerol engaged)
QPDO: PDO volumetric productivity
*Performances for strain Type 130P did not change significantly when different glycerine types were used (i.e. Novance or ADM/Greenergy blend)

These results show that the Type 130P strain bearing an intergenic mutation (in this case between the nucleotides at positions 1014234 to 1014240 on the chromosome according to *C. acetobutylicum* ATCC 824) that induces overexpression of hcpR and frdX genes surprisingly exhibits a better PDO production with higher titer and yield and a lesser residual glycerine than its parental strain, 008P.

These results also demonstrate the great advantage of the strain Type 130P which grew and produced much more PDO than the mother strain Type 008P which does not carry the genetic modification (Table 3). Indeed, all key industrial parameters (higher titer and yield of PDO and less residual glycerol) were improved for the 130P when compared to the 008P in culture conditions with industrial glycerine more toxic than usually used with Type 008P strain.

Thus, upon overexpression of the hcpR and frdX genes, the *C. acetobutylicum* DG1 pSPD5 strain produces more PDO and is more robust and therefore more suitable for an industrial process.

Example 3

Intergenic Mutation Description

Unexpectedly, a single nucleotide insertion in the intergenic region between CA_C0884 and CA_C0885 genes (illustrated in FIG. 2, SEQ ID NO: 15) has the effect of improving the production of PDO and the resistance to impurities MONG present in glycerin.

The nucleotide insertion was detected by nucleic acid sequencing of PCR fragment amplified on DNA of strain *Clostridium acetobutylicum* DG1 pSPD5 Type 008P compared to DNA of *Clostridium acetobutylicum* DG1 pSPD5 Type 130P using oligonucleotides Intergenic region forward primer (SEQ ID NO: 18) and Intergenic region reverse primer (SEQ ID NO: 19). The 'A' insertion mutation was identified in the intergenic region between CA_C0884 and CA_C0885 genes in a region of repeating 'A' nucleotide as mentioned in SEQ ID NO: 17 compared to the parental type sequence (SEQ ID NO: 16). The gene CA_C0884 hcpR (SEQ ID NO: 1) codes for a nitric oxide-responsive transcriptional regulator (SEQ ID NO: 2) and the gene CA_C0885 frdX (SEQ ID NO: 3) codes for a ferredoxin 3-like protein (SEQ ID NO: 4).

Example 4

CA_C0884 and CA_C0885 Gene Expression with or without the Intergenic Nucleotide Insertion RNA Isolation RNA was extracted from 2 ml of flask culture, transferred into a 6 ml mixture of phenol (5%)/ethanol (95%) and centrifuged at 3000 g at 4° C. for 5 minutes. Pellet was homogenized in 100 μL lysozyme 100 mg/mL, incubated 30 minutes at 37° C. and RNA was extracted using the Maxwell RSC Simply RNA Tissue kit (Promega) in a Maxwell RSC instrument (Promega).

Quantification of a Specific Ribonucleic Acid Sequence by Quantitative Reverse Transcription PCR (qRT-PCR)

As RNA cannot serve as a PCR template, the first step in gene expression profiling by qRT-PCR is the reverse transcription of the RNA template into cDNA, followed by its exponential amplification in a PCR reaction.

Reverse transcription was performed with 0.2 μg of total RNA and reverse transcribed into cDNA using SuperScript ViloIV (Invitrogen) in the presence of random primers and oligo dT primers.

The reverse transcriptase reaction was done in a total volume of 20 μl. After completion of the reaction, the mixture was held at 85° C.

Relative quantification in samples was determined by quantitative PCR using the SsoAdvanced Universal SYBR Green Supermix (Bio-rad Mitry Mory, France). Quantitative PCR was performed on a Bio-Rad C1000™ Thermal Cycler equipped with a CFX96™ Real-Time System (Bio-Rad).

PCR reactions mixtures consisted of 1×Sso Advanced Universal SYBR Green Supermix (Bio-Rad), 6 μL of a mix of forward (F) and reverse (R) primers (1 μM), 2 μL of diluted sample and nuclease free water to reach a final volume of 20 μL. Amplification was achieved according to the following thermal cycling program: initial melting at 98° C. for 2 min (1 cycle) followed by 40 cycles of melting at 98° C. for 10 sec, annealing of primers and elongation at 60° C. for 30 sec. (Melt Curve 65 to 95° C., increment 0.5° C. every 5 sec). For each experiment, threshold levels (Ct) were set during the exponential phase of the qPCR reaction using CFX Manager™ 3.1 software (Bio-rad).

The expression level of each gene was determined by quantitative reverse transcription PCR (qRT-PCR). The CA_C0884 gene based primers used were CA_C0884 gene based forward primer (SEQ ID NO:20) and CA_C0884 gene based reverse primer (SEQ ID NO:21) and the CA_C0885 gene based primers used were CA_C0885 gene based forward primer (SEQ ID NO:22) and CA_C0885 gene based reverse primer (SEQ ID NO:23). The amount of each target gene relative to the housekeeping gene DNA gyrase subunit A (gyrA: CA_C1628, primers used CA_C1628 gene based forward primer (SEQ ID NO:24) and CA_C1628 gene based reverse primer (SEQ ID NO:25) was determined for each sample using the comparative threshold cycle (Ct) method, with serial dilutions of ATCC824 genomic DNA at known concentrations used as the calibrator for each experiment. Approximately equal efficiencies of the primers were confirmed using serial dilutions of ATCC824 genomic DNA templates in order to use the comparative Ct method.

The relative expression level of both genes CA_C0884 and CA_C0885 was significantly higher in strain Type 130P carrying the intergenic mutation compared to the strain Type 008P with the parental type intergenic region (FIG. 3).

These data demonstrate that the nucleotide insertion occurring in the intergenic region between CA_C0884 and CA_C0885 of recombinant *Clostridium acetobutylicum* DG1 psPD5 strain producing PDO, allows the overexpression of the two said genes hcpR and frdX. In the presence of this mutation, PDO production performance features are improved and the strain is much more resistant to dirty, high content MONG compounds present in industrial glycerine.

REFERENCES

Altschul S, Gish W, Miller W, Myers E, Lipman D J (1990). J. Mol. Biol; 215 (3): 403-410.
Chambers et al. (1988). Gene; 68(1): 139-49.
Davis J J & Olsen G J. (2011). Mol. Biol. Evol.; 28(1):211-221.
Deml L, Bojak A, Steck S, Graf M, Wild J, Schirmbeck R, Wolf H, Wagner R. (2011).
González-Pajuelo M, Meynial-Salles I, Mendes F, Andrade J C, Vasconcelos I, and Soucaille P. 2005. Metabolic Engineering, 7: 329-336.
González-Pajuelo M, Meynial-Salles I, Mendes F, Soucaille P. and Vasconcelos I. (2006). Applied and Environmental Microbiology, 72: 96-101.
Graf M, Bojak A, Deml L, Bieler K, Wolf H, Wagner R. (2000). J. Virol.; 74(22): 10/22-10826.
Lee S, Bennett G, Papoutsakis E, (1992). Biotechnology Letters, 14(5): 427-432.
Papanikolaou S, Ruiz-Sanchez P, Pariset B, Blanchard F and Fick M. (2000), Journal of Biotechnology, 77: 191-2008.
Tummala et al. (1999). Appl. Environ. Microbiol., 65(9): 3793-3799.
Sambrook and Russell, (2001), Molecular Cloning: 3$^{rd}$ edition, Cold Spring Harbor
Vasconcelos I, Girbal L, Soucaille P., (1994), Journal of Bacteriology, 176(5): 1443-1450.

The invention claimed is:

1. A recombinant microorganism for the production of 1,3 propanediol from glycerol, wherein the recombinant microorganism converts glycerol into 1,3-propanediol and overexpresses hcpR (nitric oxide-responsive transcriptional regulator) and frdX (ferredoxin-3 like protein) genes by at least 1.5 fold as compared to an expression level in an unmodified or parental microorganism under the same conditions, and
   wherein the recombinant microorganism is *Clostridium acetobutylicum* DG1 pSPD5 and said hcpR and frdX genes are overexpressed by a genetic modification comprising at least one of the following: mutating the promoter regulating the expression of the hcpR and frdX genes, mutating the intergenic region between the hcpR and frdX genes, gene duplication, or overexpressing the hcpR and frdX genes from a plasmid.

2. The recombinant microorganism of claim 1, wherein the recombinant microorganism is adapted to grow on a culture medium having a glycerol concentration in the industrial glycerine which is comprised between 90 g/L and 120 g/L and/or wherein the industrial glycerine comprises at least 5% fatty acids.

3. A method for the fermentative production of 1,3-propanediol, wherein the recombinant microorganism as set forth in claim 1 is cultured on a medium comprising industrial glycerine.

4. The method of claim 3, wherein the hcpR and frdX genes are overexpressed in the recombinant microorganism by intergenic mutation between the hcpR and frdX genes by insertion.

5. The method of claim 4, wherein the insertion occurs in a region of repeating A nucleotides.

6. The method of claim 3, wherein the recombinant microorganism is adapted to grow in the presence of a glycerol concentration in the industrial glycerine which is comprised between 90 g/L and 120 g/L.

7. The method of claim 6, wherein the industrial glycerine comprises at least 5% fatty acids.

8. The method of claim 3, wherein the industrial glycerine is a by-product of biodiesel production.

9. The method of claim 3, wherein the 1,3 propanediol produced in the culture is further purified.

* * * * *